(12) United States Patent
Kinoshita et al.

(10) Patent No.: US 9,028,427 B2
(45) Date of Patent: May 12, 2015

(54) GUIDE WIRE

(75) Inventors: Yasushi Kinoshita, Fujinomiya (JP);
Junichi Kobayashi, Fujinomiya (JP);
Tadashi Kousai, Fujinomiya (JP)

(73) Assignee: Terumo Kabushiki Kaisha,
Shibuyka-Ku, Tokyo (JP)

( * ) Notice: Subject to any disclaimer, the term of this patent is extended or adjusted under 35 U.S.C. 154(b) by 670 days.

(21) Appl. No.: 12/354,208

(22) Filed: Jan. 15, 2009

(65) Prior Publication Data

US 2009/0163833 A1    Jun. 25, 2009

Related U.S. Application Data

(63) Continuation-in-part of application No. 12/048,664, filed on Mar. 14, 2008, now Pat. No. 8,187,206.

(60) Provisional application No. 61/006,644, filed on Jan. 24, 2008.

(30) Foreign Application Priority Data

| Mar. 14, 2007 | (JP) | ................................. 2007-065890 |
| Mar. 23, 2007 | (JP) | ................................. 2007-077917 |
| Jan. 18, 2008 | (JP) | ................................. 2008-009723 |
| Jan. 18, 2008 | (JP) | ................................. 2008-009726 |

(51) Int. Cl.
*A61B 5/00* (2006.01)
*A61M 25/00* (2006.01)
*A61M 25/09* (2006.01)

(52) U.S. Cl.
CPC ....... *A61M 25/09* (2013.01); *A61M 2025/0008* (2013.01); *A61M 2025/09075* (2013.01);

(Continued)

(58) Field of Classification Search
USPC .......................................................... 600/585
See application file for complete search history.

(56) References Cited

U.S. PATENT DOCUMENTS 4,447,239 A * 5/1984 Krutten ......................... 604/529
4,867,174 A   9/1989 Skribiski
(Continued)

FOREIGN PATENT DOCUMENTS

| DE | 198 29 620 A1 | 2/1999 |
| EP | 0 771 572 A1  | 5/1997 |

(Continued)

OTHER PUBLICATIONS

Office Action issued by the European Patent Office on Jun. 12, 2012 in corresponding European Patent Application No. 09 702 905.2-1526.

(Continued)

*Primary Examiner* — Devin Henson
(74) *Attorney, Agent, or Firm* — Buchanan Ingersoll & Rooney PC

(57) ABSTRACT

A guide wire includes an elongate wire body, and a marker at least at a distal-side portion of the wire body over the whole circumference to indicate the intracorporeal position of the wire body. The marker has a first line-forming portion and a second line-forming portion which intersect each other at a plurality of locations so that the marker has a grid-like shape as a whole. According to another aspect, a guide wire includes a member with a core wire, a marker-forming layer partly encircling the outer surface of the member and differing in color from the member, and a coating layer covering the marker-forming layer and the member at least in the marker-forming layer region and having transparency making the marker-forming layer visible. The marker-forming and coating layers can be formed from mutually miscible resins, while the marker-forming layer functions as a visible marker.

27 Claims, 23 Drawing Sheets

(52) U.S. Cl.
CPC ............... *A61M2025/09091* (2013.01); *A61M 2025/09108* (2013.01); *A61M 2025/09133* (2013.01); *A61M 2205/6081* (2013.01)

(56) References Cited

U.S. PATENT DOCUMENTS

| | | | |
|---|---|---|---|
| 5,084,022 A | | 1/1992 | Claude |
| 5,379,779 A * | | 1/1995 | Rowland et al. ............ 600/585 |
| 5,479,938 A | | 1/1996 | Weier |
| 5,695,483 A * | | 12/1997 | Samson .................... 604/526 |
| 5,827,201 A * | | 10/1998 | Samson et al. ............ 600/585 |
| 6,251,085 B1 | | 6/2001 | Tezuka |
| 6,354,989 B1 | | 3/2002 | Nudeshima |
| 6,613,002 B1 * | | 9/2003 | Clark et al. ............... 600/593 |
| 6,811,958 B2 | | 11/2004 | Iwami et al. |
| 2004/0039308 A1 | | 2/2004 | Murayama et al. |
| 2004/0167438 A1 * | | 8/2004 | Sharrow .................... 600/585 |
| 2006/0015040 A1 * | | 1/2006 | Yunoki et al. ............. 600/585 |
| 2006/0047224 A1 * | | 3/2006 | Grandfield ................. 600/585 |
| 2006/0116609 A1 | | 6/2006 | Kanuka et al. |
| 2006/0149165 A1 * | | 7/2006 | Kennedy et al. ........... 600/585 |
| 2007/0149037 A1 | | 6/2007 | Souba et al. |
| 2008/0228109 A1 | | 9/2008 | Kinoshita et al. |

FOREIGN PATENT DOCUMENTS

| | | |
|---|---|---|
| EP | 1 203 595 A1 | 5/2002 |
| EP | 1 348 461 A2 | 10/2003 |
| EP | 1 607 035 A1 | 12/2005 |
| JP | 01-148273 | 6/1989 |
| JP | 10-099442 A | 4/1998 |
| JP | 2000-116802 | 4/2000 |
| JP | 2001-046508 A | 2/2001 |
| JP | 2001-340288 | 12/2001 |
| JP | 2002-017864 | 1/2002 |
| JP | 2004-000455 | 1/2004 |
| JP | 2004-130123 | 4/2004 |
| JP | 2004-229947 A | 8/2004 |
| JP | 2004-265195 | 9/2004 |
| JP | 2007-097662 A | 4/2007 |
| JP | 2008-264498 A | 11/2008 |
| WO | WO 00/74565 A1 | 12/2000 |
| WO | WO 2004/084712 A1 | 10/2004 |
| WO | WO 2006/065909 A1 | 6/2006 |

OTHER PUBLICATIONS

Canadian Office Action dated Feb. 3, 2012, issued in corresponding Canadian Patent Application No. 2,712,150.

European Search Report issued Jun. 29, 2011 by the European Patent Office in European Application No. 09702905.2.

Korean Office Action issued Jan. 20, 2014 in corresponding Korean Patent Application No. 10-2012-7005382 with attached certification statement.

* cited by examiner

GUIDE WIRE

This application is a continuation-in-part of U.S. application Ser. No. 12/048,664 filed on Mar. 14, 2008 and entitled "Guide Wire," the entire content of which is incorporated herein by reference. This application also claims the benefit of U.S. Provisional Application No. 61/006,644 filed on Jan. 24, 2008, the entire content of which is incorporated herein by reference.

TECHNICAL FIELD

The present invention relates to a guide wire. More particularly, the present invention relates to a guide wire (or a transendoscopic guide wire) to be inserted into a living organism through an endoscope.

BACKGROUND DISCUSSION

A guide wire is used to facilitate insertion of a catheter into a lumen (such as digestive tract and blood vessel) of a living body. It leads a catheter slipped thereon to a desired position in a lumen.

A guide wire is also used to lead a catheter to a desired position in a lumen of a living body through an endoscope or a lumen of an endoscope at the time of observation or treatment of a lumen of a living body.

A guide wire for this purpose has a marker on its surface which tells its position and movement during insertion. A guide wire in a single color without a marker cannot be recognized for its movement when it turns around its axis. There have been proposed several methods for attaching a marker to a guide wire.

One method is described in U.S. Pat. No. 5,379,779 and involves slipping a hollow tube of polytetrafluoroethylene (PTFE), having one or more colored spiral pattern, onto a core wire and subsequently allowing it to be heat-shrink around the core wire of a guide wire.

Another method described in U.S. Pat. No. 6,811,958 involves adding a color producing agent (such as mica which produces a color upon irradiation with a laser beam) to the covering layer on the core of the guide wire and irradiating the covering layer with a laser beam for color development, thereby forming a marker as desired.

The above-mentioned guide wires include those which have surface irregularities formed thereon.

An example is disclosed in U.S. Patent Application Publication No. 2006/116609 in which the guide wire has a curved part on which surface irregularities are formed so as to make it more flexible. This guide wire has its surface irregularities formed from the outermost layer which is partly removed by heating a coil wound around the curved part at prescribed intervals.

In addition, observation or treatment of an intracorporeal lumen or the like by use of an endoscope is also known, and a guide wire is again used by which the endoscope or a catheter inserted in the lumen of the endoscope is guided to the target site of the intracorporeal lumen or the like.

During insertion of the guide wire, the guide wire is moved along the axial direction thereof while it is rotated about its axis. These operations are carried out while visually checking the guide wire under fluoroscopy or through an endoscope. If the guide wire is monochromatic, it cannot be seen whether or not the guide wire is moved as intended. Some guide wires are provided at their surfaces with markers (marks) for indicating the position or the like. An example is disclosed in Japanese Patent Laid-open No. 2001-46508. Here, the guide wire mark is helical.

During use of the guide wire described in the aforementioned document, whether the guide wire is moved along its axial direction or rotated about its axis, each portion of the helical mark which is visually checked in practice (each belt-like portion cross-hatched in FIG. 3(b) of the document) appears to be moving to change in one direction, for example, in the distal direction. Therefore, even when the guide wire is rotated about its axis by applying torque, the operator might perceive that the guide wire is moving distally or proximally, contrary to what was intended, and this may cause a mis-steering of the guide wire.

SUMMARY

A guide wire positionable in a patient's body comprises an elongate wire member possessing a circumference and a longitudinal extent from a distal end of the wire member to a proximal end of the wire body, and a first line-forming marker portion which is visible exteriorly of the patient's body when the guide wire is positioned in the patient's body, the first line-forming marker portion extending helically around the outer circumference of a first part of the longitudinal extent of the wire member in a first rotational direction, and the first line-forming marker portion extending circumferentially around the wire member plural times, with adjacent windings of the first line-forming marker portion being spaced apart from one another. In addition, the guide wire includes a second line-forming marker portion which is visible exteriorly of the patient's body when the guide wire is positioned in the patient's body to indicate with the first line-forming marker portion an intracorporeal position of the guide wire, wherein the second line-forming marker portion extends helically around the outer circumference of the first part of the longitudinal extent of the wire member in a second rotational direction opposite the first rotational direction, with the second line-forming marker portion extending circumferentially around the wire member plural times, with adjacent windings of the second line-forming marker portion being spaced apart from one another. The first line-forming marker portion intersects the second line-forming marker portion at a plurality of spaced apart locations, and portions of the first part of the longitudinal extent of the wire member are uncovered by the first line-forming marker portion and the second line-forming marker portion.

According to another aspect, a guide wire positionable in a patient's body comprises an elongate wire member possessing a circumference and a longitudinal extent extending from a distal end of the wire member to a proximal end of the wire body, and a marker visible exteriorly of the patient's body when the guide wire is positioned in the patient's body to indicate an intracorporeal position of the wire body, wherein the marker is located on the wire member, extends along at least a portion of the longitudinal extent of the wire member and extends over an entirety of the circumference of the portion of the longitudinal extent of the wire member. The marker comprises a first line-forming portion and a second line-forming portion which intersect each other at a plurality of locations so that the marker possesses an overall grid shapes arrangement of the first and second line-forming portions.

A further aspect involves a method of fabricating a guide wire configured and dimensioned to be positioned in a patient's body. The method includes masking a portion of an elongated wire member with a first mask to leave a helically extending unmasked first portion, applying a pigment-containing first resin to the unmasked first portion of the wire member, removing the first mask, whereby the pigment-containing first resin remains on the wire member and forms a helically extending first line-forming marker portion, masking a portion of the elongated wire member with a second mask to leave a helically extending unmasked second portion, applying a pigment-containing second resin to the unmasked second portion of the wire member, and removing the second mask, whereby the pigment-containing second resin remains on the wire member and forms a helically extending second line-forming marker portion. The first and second line-forming marker portions intersect one another at a plurality of spaced apart intersection points so that portions of the wire member are uncovered by the first and second line-forming marker portions, the first and second line-forming marker portions together forming a marker visible exteriorly of the patient's body when the guide wire is positioned in the patient's body to indicate an intracorporeal position of the wire body.

BRIEF DESCRIPTION OF THE DRAWING FIGURES

DETAILED DESCRIPTION

Figure 1:
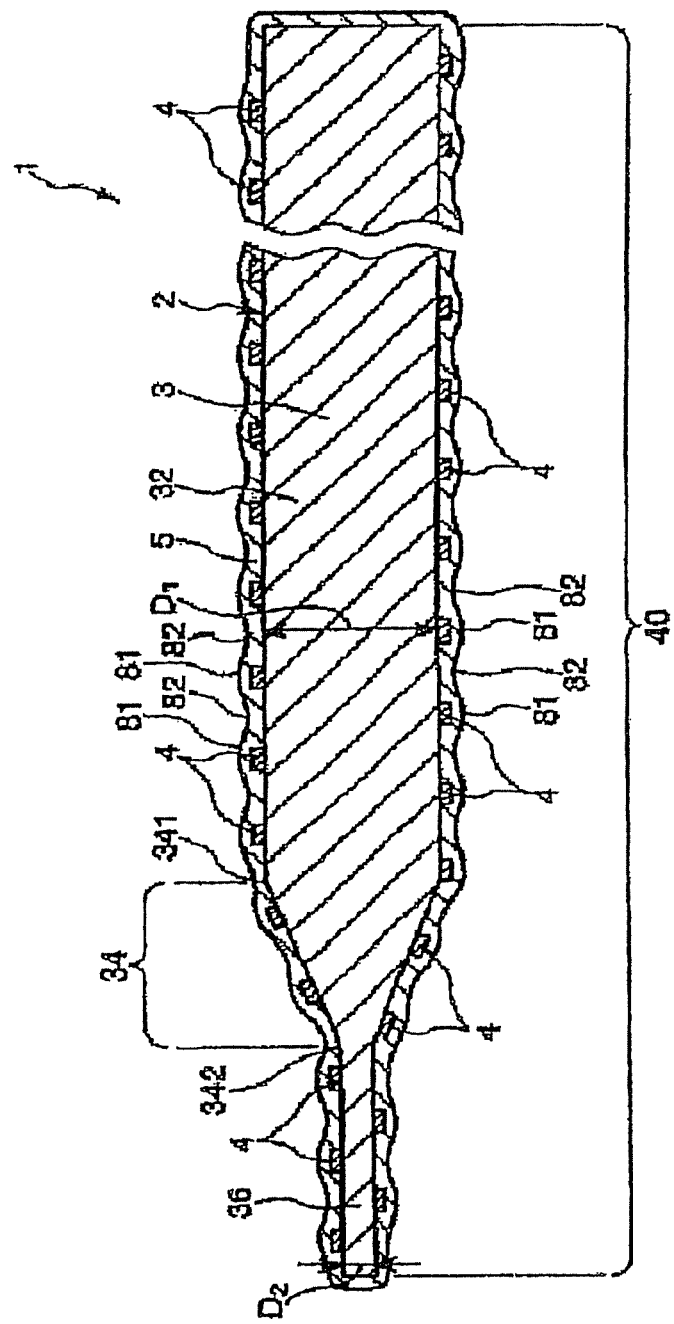
FIG. 1 is a longitudinal cross-sectional view of a first embodiment of the guide wire disclosed here.
Figure 2:
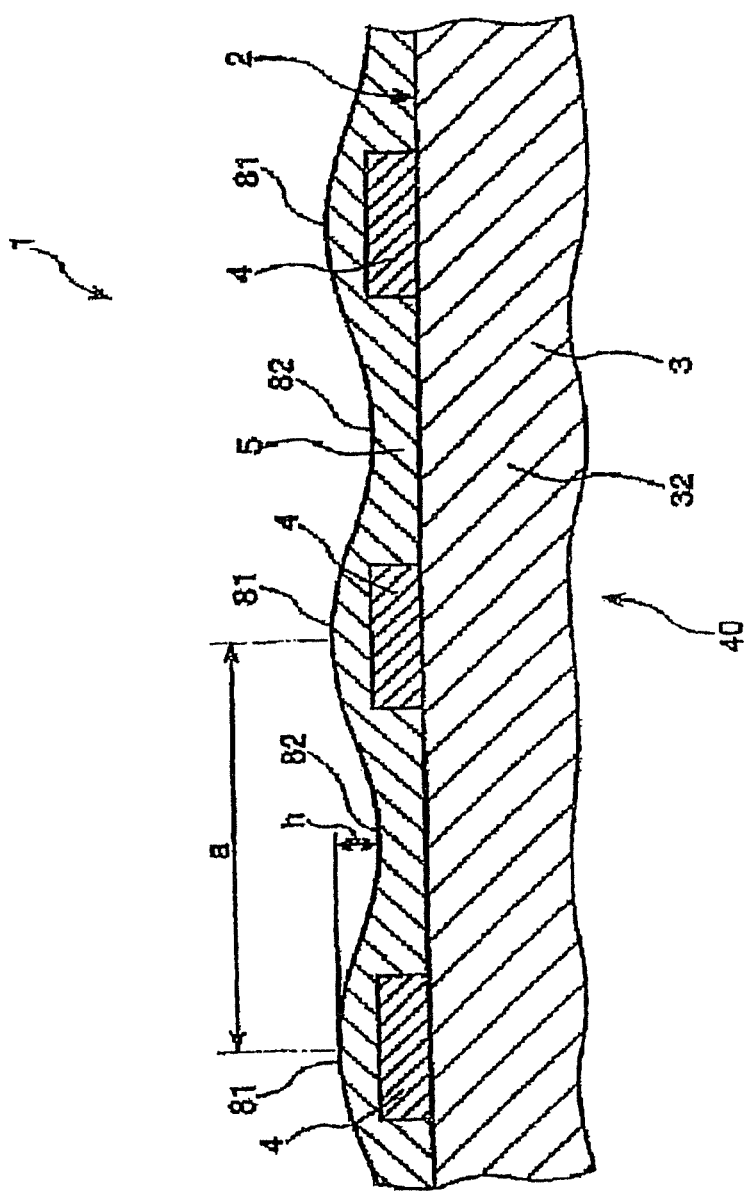
FIG. 2 is a partial longitudinal cross-sectional view of the part of the FIG. 1 guide wire near the outer surface of the guide wire.

FIGS. 1 and 2 illustrate a guide wire according to one disclosed embodiment. It is to be understood that the guide wire is illustrated in FIG. 1 in a manner intended to facilitate an understanding of the guide wire, and so the guide wire is depicted with its length shortened and its thickness exaggerated. Therefore, the illustration is different from actual in the ratio of thickness to length. For the sake of convenience in description, the right and left sides in FIG. 1 are designated as "base end" and "forward end," respectively.

As shown in FIG. 1, the guide wire 1 includes a member 2, a bulge-forming layer 4, and a coating layer 5. The member 2 is a flexible core wire 3. The bulge-forming layer 4 differs in color from the member 2 (core wire 3) and results in the outer surface of the guide wire 1 possessing a bulge. The coating layer 5 possesses a transparency (light transmission) which makes the bulge-forming layer 4 visible.

According to this embodiment, the member 2 is a single continuous core wire 3 and has a round cross-section. However, the member 2 may be composed of two or more different or identical core wires joined together by welding or brazing. It may also have any additional structure.

The guide wire 1 is not specifically restricted in its overall length. A preferred overall length is about 200 to 5,000 mm. Also, the guide wire is not specifically restricted in outside diameter. A preferred outside diameter is about 0.2 to 1.2 mm.

The core wire 3 extends over the entire length of the guide wire 1. The core wire includes a main part 32 (which corresponds to the main body of the guide wire 1), a tapered part 34 (which is close to the forward end, closer to the forward end than the rearward end), and a relatively thin part 36 (at the forward end). The main part 32 has a nearly constant outside diameter. The tapered part 34 gradually decreases in outside diameter toward the forward end. The relatively thin part 36 has a nearly constant outside diameter.

The tapered part 34 results in the core wire 3 gradually (continuously in the illustrated embodiment) increasing in flexibility in a direction from the boundary (or the base end 341 of the tapered part) between the main part 32 and the tapered part 34 toward the forward end. This adds flexibility to the guide wire 1, thereby making it relatively easy and safe to insert the guide wire 1 into a living body.

The relatively thin part 36 extends from the tapered part 34 to the forward end of the guide wire and is more flexible than the rest of the guide wire.

The main part 32 of the core wire 3 has an outside diameter D1 (measured at the base end 341 of the tapered part), which is not specifically restricted but should preferably be about 0.3 to 1.0 mm, more preferably about 0.4 to 0.7 mm.

The relatively thin part 36 of the core wire 3 has an outside diameter D2 (measured at the forward end 342 of the tapered part), which is not specifically restricted but should preferably be about 0.05 to 0.3 mm, more preferably about 0.1 to 0.2 mm. The outside diameter of the relatively thin part 36 may be constant or may gradually decrease in a direction toward the forward end.

The length of the tapered part 34 may vary depending on the use of the guide wire and the kind of guide wire. Though not limited in this regard, the length of the tapered part 34 should preferably be about 10 to 300 mm, more preferably about 30 to 250 mm.

The length of the relatively thin part 36 is also not specifically restricted. Nevertheless, it should preferably be about 0 to 100 mm, more preferably about 10 to 50 mm.

The outside diameter of the tapered part 34 may decrease at a constant rate or a varying rate along the lengthwise direction of the core wire 3 (the member 2). Also, there may be two or more of the tapered part 34.

The core wire 3 should preferably have minute surface irregularities. This is true particularly for that part of the outer surface (immediately under the coating layer 5) where the bulge-forming layer 4 in the bulge-forming region 40 (mentioned later) is not yet formed. The minute surface irregularities (which are sufficiently small compared with the bulging part 81 and recessed part 82 mentioned later) improve adhesion between the core wire 3 and the coating layer 5, thereby inhibiting or preferably preventing the coating layer 5 from peeling off.

The core wire 3 may be made of metallic materials, such as stainless steel, Ni—Ti alloy, Ni—Al alloy, Cu—Zn alloy, and other superelastic alloys, or resin materials having a comparatively high stiffness. They may be used alone or in combination with one another.

The guide wire 1 disclosed here is not specifically restricted in its application. It may be used, for example, to guide a catheter to a desired position (such as a cavity in a living body) through the lumen of an endoscope. A guide wire used in this manner is referred to as a "transendoscopic guide wire." The embodiment mentioned below is concerned typically with the case in which the guide wire 1 is used as a transendoscopic guide wire.

The transendoscopic guide wire has a visible marker on its outer surface, so that the marker is visible through the endoscope. In this embodiment, the bulge-forming layer 4 functions not only as a means for causing the outer surface of the guide wire 1 to partly bulge (or means for arranging both the bulging part 81 and the recessed part 82) but also as the visible marker. The outer surface of the guide wire 1 has a plurality of bulging parts and non-bulging parts.

As mentioned, the guide wire 1 includes the bulge-forming region 40 in which the bulge-forming layer 4 is formed. On the outer layer of the core wire 3 (or the member 2) in the bulge-forming region 40 is a portion of the bulge-forming layer 4. The bulge-forming layer 4 differs in color from the outer surface of the core wire 3 (or the member 2), so that it functions as the visible marker or a marker layer.

The bulge-forming region 40 may extend entirely or partly (along the overall length) in the lengthwise direction of the core wire 3. In this embodiment, the bulge-forming region 40 extends over the entire length of the core wire 3 from the proximal end of the core wire 3o the distal end of the core wire 3.

The bulge-forming region 40, which is formed on at least a part of the core wire 3, should at least extend from the forward end of the core wire 3 to the midway of the core wire 3. The length of the bulge-forming region 40 in the lengthwise direction should preferably be 5 cm or longer, more preferably about 10 to 50 cm, most preferably about 20 to 40 cm.

The bulge-forming layer 4 may be formed from a material containing a resin and a pigment. The color of the bulge-forming layer 4 depends mainly on the kind, amount, and properties of the pigment contained therein and also on the composition and properties (especially color) of the resin material contained therein. Any color can be produced by an adequate or appropriate combination.

The color of the bulge-forming layer 4 is important so that the operator can observe the movement of the guide wire 1 through the endoscope. An adequate color should be selected in view of the color of the core wire 3 (or the member 2) underneath.

To cite an example, the core 3 or its oxide coating film may have a silver white color (metallic color) or a grayish or black color, and the bulge-forming layer 4 may have a reddish or yellowish color. In this case there is a large difference in brightness between them, which gives rise to a high contract. Thus the bulge-forming layer 4 is highly visible, which is desirable. Another case in which they have complementary colors is also desirable because of the high visibility of the bulge-forming layer 4. A high contrast is obtained when a dark color such as black (or other dark colors such as charcoal gray, dark brown, navy blue, and violet) is combined with a light color (such as yellow, yellowish green, and orange), or when blue is combined with red, orange, or pink. A high contrast is also obtained by a combination of the same colors differing in shade, such as dark blue with light blue and reddish-brown with pink.

The constituent material of the bulge-forming layer 4 preferably contain any one of resins (1) and (2) listed below.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, polyethersulfone, and fluororesin, such as polytetrafluoroethylene (PTFE) and ethylene-tetrafluoroethylene copolymer (ETFE). They may be used alone or in combination with one another.

(2) Thermosetting Resins

Examples of the thermosetting resins include epoxy resin, phenolic resin, unsaturated polyester resin, polyimide resin, silicone resin, and polyurethane resin. They may be used alone or in combination with one another. The bulge-forming layer 4 as a whole should contain pigment in an amount of about 10 to 99 wt %, preferably about 50 to 95 wt %, to produce desired colors. An adequate amount depends on the type and properties of the pigment and the composition and properties of the resin material. The bulge-forming layer 4 should preferably contain pigment uniformly distributed therein, although uneven distribution in its outer surface is permissible.

Pigments may be used alone or in combination with one another in the form of a mixture.

The bulge-forming layer 4 is not specifically restricted in shape (pattern) and dimensions. It depends on the shape (pattern) of the bulging part 81 and the recessed part 82 to be formed. However, it should preferably have a thickness of about 1 to 30 μm, more preferably about 2 to 10 μm, so that the guide wire 1 can be made relatively thin.

As shown in the figure, the bulge-forming layer 4 takes on a spiral pattern. The spiral (or circular) pattern should preferably have a width (i.e., the width of the bulge-forming layer 4) of about 0.3 to 10 mm and a pitch (gap) of about 0.5 to 10 mm.

The shape of the bulge-forming layer 4 is not restricted to spiral or circular. Any shape is acceptable so long as it is visible if the bulge-forming layer is to function as a visible marker. It may be a continuous line with a visible width or a discontinuous pattern with a visible area. It includes, for example, straight line, wavy pattern, polka dots, check pattern, and mesh pattern. It also includes numerals, letters, symbols, and graduations, which are visible. Two or more different patterns may be combined with each other (for example, a spiral pattern and a circular pattern placed on top of the other) for better visibility.

The pigment may be either an inorganic pigment(s) or an organic pigment(s), with the former being preferable because of their good heat resistance. Inorganic pigments include carbon black, mica, titanium dioxide, nickel-titanium yellow, prussian blue, milori blue, cobalt blue, ultramarine, and viridian blue.

The coating layer 5 has such transparency as to make the bulge-forming layer 4 visible. It covers the bulge-forming layer 4 and the core wire 3 (or the member 2) in at least the bulge-forming region 40. In this embodiment, the coating layer 5 covers the bulge-forming layer 4 and the entire length of the core wire 3.

The outer surface of the coating layer 5 (or the outer surface of the guide wire 1) has the part where the bulge-forming layer 4 is formed and the part where the bulge-forming layer 4 is not formed, the former bulging relative to the latter. In other words, the part where the bulge-forming layer 4 is formed is the bulging part 81, and the part where the bulge-forming layer 4 is not formed is the recessed part 82. Since the coating layer 5 is comparatively thin, the outer surface of the coating layer 5 bulges in conformity with the shape and pattern of the bulge-forming layer 4.

This structure reduces the area of contact between the outer surface of the coating layer 5 and the lumen of the catheter or the lumen of the endoscope, and also reduces frictional resistance (or sliding resistance), thereby improving the operability of the guide wire 1.

The bulging part 81 and the recessed part 82 are not formed by directly fabricating the coating layer 5, but they result from the bulge-forming layer 4 immediately under the coating layer 5. Therefore, the outer surface of the coating layer 5 is smooth without sharp angles and projections. In other words, the bulging part 81 and the recessed part 82 have their corners rounded. This structure improves slidability and contributes to higher safety.

The bulging part 81 and the recessed part 82 are not specifically restricted in shape and pattern. However, in the illustrated structure, the bulging part 81 possesses a spiral pattern.

In the case where the bulging part 81 and the recessed part 82 in spiral or circular pattern are formed alternately along the lengthwise direction of the core wire 3 (member 2), they should be separated from each other at intervals (a) of about 0.5 to 10 mm, preferably about 1 to 5 mm.

The bulging part 81 should have an average height (h) of about 1 to 30 μm, preferably 2 to 10 μm.

The coating layer 5 is formed from a resin-containing material.

The constituent material of the coating layer 5 may contain any resin which is not specifically restricted. At least one of the resins should be the one which is miscible with the resin contained in the constituent material of the bulge-forming layer 4. In other words, mutually miscible resins should be contained in the constituent material for the coating layer 5 and the constituent material for the bulge-forming layer 4. This ensures firm adhesion between the bulge-forming layer 4 and the coating layer 5, thereby preventing the coating layer 5 from peeling off even when the guide wire 1 experiences repeated bending and twisting.

"Miscibility" means that the two components are able to well dissolve each other thermodynamically. In other words, they do not separate from each other after curing.

Mutually miscible resins may be the same resins or different resins. Examples of combinations of different resins include polyamideimide and polyimide, polyetherimide and polyimide, polyamideimide and polyetherimide, or polysulfone and polyethersulfone, which have common groups, such as imide and sulfone.

The content of the mutually miscible resins in the bulge-forming layer 4 should preferably be about 1 to 90 wt %, more preferably about 5 to 50 wt %, based on the total weight of the bulge-forming layer 4, for good adhesion between the bulge-forming layer 4 and the coating layer 5. The content of the mutually miscible resins in the coating layer 5 should preferably be about 1 to 50 wt %, more preferably about 3 to 35 wt %, based on the total weight of the coating layer 5, for good adhesion between the bulge-forming layer 4 and the coating layer 5.

The coating layer 5 is not specifically restricted in thickness. It should preferably have a thickness of about 1 to 20 μm, more preferably about 2 to 10 μm, depending on the dimensions of the bulging part 81 and the recessed part 82.

The total thickness of the coating layer 5 and the bulge-forming layer 4 at the bulging part 81 is not specifically restricted; it should be 50 μm or smaller, preferably about 2 to 40 μm, more preferably about 4 to 20 μm.

The foregoing thickness is necessary for the guide 1 to have a small diameter. This object is not achieved with the conventional visible marker, which is formed by covering the core wire with a heat-shrinkable tube (as thick as about 100 μm) having a spiral or parallel stripy pattern. In this embodiment, the bulge-forming layer 4 and the coating layer 5 having the foregoing thickness can be formed relatively easily and certainly by using the structure (mentioned above) and the production method (mentioned later).

The method for producing the guide wire 1 is not described in detail here, but will be described later together with the method for producing the guide wire 1 according to the second embodiment.

As mentioned above, the guide wire 1 according to the first embodiment has the bulged part 81 and the recessed part 82 formed on the outer surface of the guide wire. As mentioned, this structure reduces the area of contact between the outer surface of the coating layer 5 and the inside of the catheter or the lumen of the endoscope, and also reduces frictional resistance (or sliding resistance), thereby improving the operability of the guide wire 1.

The bulging part 81 and the recessed part 82 are not formed by directly fabricating the coating layer 5, but result from the bulge-forming layer 4 located immediately under the coating layer 5. Therefore, the outer surface of the coating layer 5 is smooth without sharp angles and projections. In other words, the bulging part 81 and the recessed part 82 have their corners rounded. This structure helps improve slidability and contribute to higher safety.

The guide wire 1 according to the first embodiment has a relatively small diameter, and the bulge-forming layer 4 has any desired color owing to adequate selection of pigment and resin material (for composition and amount) contained therein. The bulge-forming layer 4 allows a wide selection of colors for any color of the core wire 3 (or the member 2). Therefore, the resulting guide wire 1 has an easily visible marker.

Since the coating layer 5 and the bulge-forming layer 4 are formed from mutually miscible resins, they firmly adhere to each other and the coating layer 5 remains without peeling off even when the guide wire 1 experiences bending and twisting repeatedly.

According to this embodiment, the bulge-forming layer 4 may not function as a visible marker. In this case the bulge-forming layer 4 is not required to contain any pigment. In other words, the bulge-forming layer 4 may have the same color as the core wire 3 (or the member 2), or it may be transparent or opaque. In addition, the coating layer 5 may also be transparent, and the bulge-forming layer 4 may have a shape which does not allow the recognition of its position.

According to this embodiment, the member 2 is formed from the core wire 3, and the bulge-forming layer 4 and the coating layer 5 are formed directly on the outer surface of the core wire 3. However, the guide wire disclosed here is not limited to this structure. For example, the core wire 3 may have on its outer surface one or more layers and may further have the bulge-forming layer 4 and the coating layer 5 on such layers. In this case, the member 2 has one or more layers on the outer surface of the core wire 3 such that they cover the outer surface partly or entirely.

Figure 3:
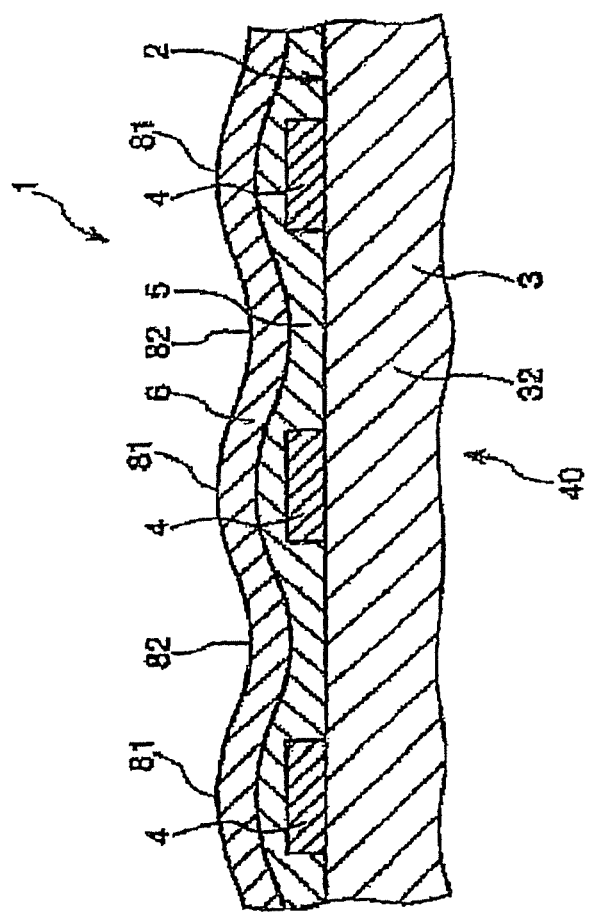
FIG. 3 is a partial longitudinal cross-sectional view of a part of a guide wire near the outer surface of the guide wire according to a second embodiment.
Figure 4:
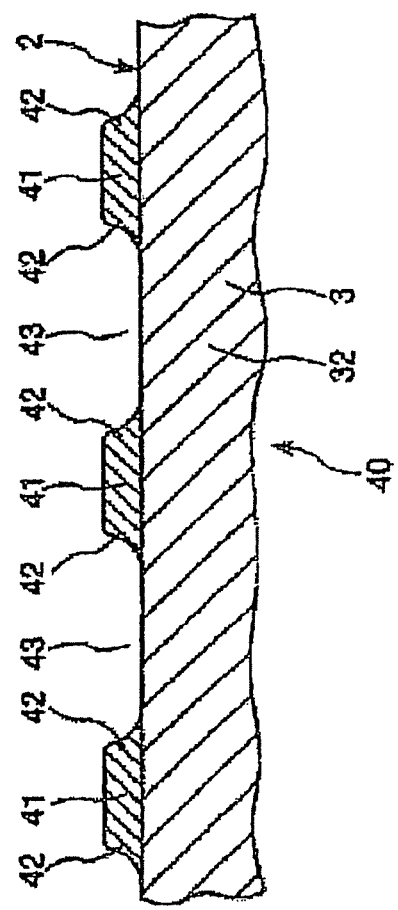
FIG. 4 is a partial longitudinal cross-sectional view of a part of the guide wire near the outer surface of the guide wire, illustrating a method for producing the guide wire shown in FIG. 3.

FIG. 3 illustrates a part of the guide wire near the outer surface of the guide wire in a second embodiment, while FIG. 4 shows a part near the outer surface of the guide wire. FIG. 4 is intended to illustrate a method for producing the guide wire shown in FIG. 3.

The guide wire 1 according to the second embodiment is described below. The description primarily describes differences between this embodiment and the first embodiment. Features in this embodiment that are common to the first embodiment are identified with the same reference numerals and a detailed description of such features is not repeated.

As shown in FIG. 3, the guide wire 1 according to the second embodiment has an outer layer 6 which covers the coating layer 5. This outer layer 6 possesses a transparency allowing the bulge-forming layer 4 to be visible. The outer layer 6 may cover the coating layer 5 partly or entirely (throughout the entire length). The outer surface of the outer layer 6 (or the outer surface of the guide wire 1) has the part where the bulge-forming layer 4 is formed and the part where the bulge-forming layer 4 is not formed, the former bulging relative to the latter, so that the bulging part 81 and the recessed part 82 are formed.

The outer layer 6 may be formed for various purposes. One purpose is to reduce the friction (sliding resistance) or improve the slidability of the guide wire 1, which contributes to the operability of the guide wire 1.

For the guide wire 1 to have reduced friction (sliding resistance), the outer layer 6 should be formed from a material which contains a resin (or a second resin) that reduces friction as mentioned below. As a result, the guide wire 1 decreases in friction (sliding resistance) with the lumen of the catheter (which is used in combination with the guide wire 1) and also with the lumen of the endoscope, which leads to improved operability. The reduced sliding resistance helps inhibit or preferably prevent the guide wire 1 from kinking when the guide wire 1 is moved or rotated in the lumen of the catheter or in the lumen of the endoscope.

The thickness of the outer layer 6 is not specifically restricted; it is usually about 1 to 15 µm, preferably about 2 to 10 µm. An excessively large thickness might physically affect the guide wire 1 and it is disadvantageous for the guide wire 1 to have a too-small diameter.

The bulge-forming layer 4 of the guide wire 1 is formed from a material containing a first resin and a pigment. And, the coating layer 5 is formed from a material containing a resin miscible with the first resin and a second resin differing from the miscible resin. Preferably, it should be formed from a material containing the first resin and a second resin differing from the first resin. Also, the outer layer 6 is formed from a material containing a resin miscible with the second resin, preferably a material containing the second resin.

Thus, the coating layer 5 functions as an adhesive layer (or adhesive) to bond the bulge-forming layer 4 and the outer layer 6 together. Therefore, even though the second resin contained in the outer layer 6 is one which hardly adheres to other members, the outer layer 6 protects itself from peeling. In other words, since the coating layer 5 and the bulge-forming layer 4 are formed from materials containing mutually miscible resins (or the first resin which is common to them), the bulge-forming layer 4 and the coating layer 5 firmly adhere (bond) to each other. In addition, since the outer layer 6 and the coating layer 5 are formed from the second resin which is common to them, the coating layer 5 and the outer layer 6 firmly adhere to each other. Thus, the coating layer 5 and the outer layer 6 protect themselves from peeling even when the guide wire 1 experiences bending and twisting repeatedly.

The bulge-forming layer 4 as a whole may contain the first resin in an amount about 1 to 90 wt %, preferably about 5 to 50 wt %, so that good adhesion is achieved between the bulge-forming layer 4 and the coating layer 5.

The coating layer 5 as a whole may contain a resin (e.g., the first resin) which is miscible with the first resin in the coating layer 5 in an amount of about 1 to 50 wt %, preferably about 3 to 35 wt %, so that good adhesion is achieved between the bulge-forming layer 4 and the coating layer 5.

The coating layer 5 as a whole may contain the second resin in an amount more than 50 wt %, preferably about 50 to 99 wt %, more preferably about 65 to 97 wt %, so that good adhesion is achieved between the coating layer 5 and the outer layer 6.

The outer layer 6 as a whole may contain the second resin in an amount of about 1 to 30 wt %, preferably about 3 to 20 wt %, or the outer layer 6 may be formed from a resin miscible with the second resin; for example the outer layer 6 can be made entirely of the second resin material, so that good adhesion is achieved between the coating layer 5 and the outer layer 6 and the guide wire 1 has reduced friction (or sliding resistance).

The first resin preferably is any one of resins (1) and (2) listed below.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin to make the guide wire 1 decrease in friction (or sliding resistance) includes fluororesins, such as polytetrafluoroethylene (PTFE), ethylene-tetrafluoroethylene copolymer (ETFE), and tetrafluoroethylene-perfluoroalkylvinyl ether copolymer (PFA).

The following is a description of the method for producing the guide wire 1. This method, used to fabricate the second embodiment of the guide wire shown in FIGS. 3 and 4, can also be used to fabricate the first embodiment of the guide wire, except for the step pertaining to the formation of the outer layer 6.

(1) The first step is to prepare a liquid material for the bulge-forming layer 4 (composed of the constituent of the bulge-forming layer 4 and a solvent), a liquid material for the coating layer 5 (composed of the constituent of the coating layer 5 and a solvent), and a liquid material for the outer layer 6 (composed of the constituent of the outer layer 6 and a solvent).

Next, the liquid material for the bulge-forming layer 4 is applied to the bulge-forming region 40 on the outer surface of the core wire 3 (or the member 2), so that a coating film is formed entirely on the bulge-forming region 40. The coating film is dried.

Incidentally, the bulge-forming layer 4, the coating layer 5, and the outer layer 6 should have the appropriate thickness and other dimensions such as mentioned above by way of example.

(2) The coating film formed from the liquid material for the bulge-forming layer 4 is partly removed so that the bulge-forming layer 4 has a desired pattern.

The coating film should preferably be removed in such a way as to form fine surface irregularities in that part of the outer surface of the core wire 3 from which the coating film is removed (or the surface directly under the coating layer 5 at the part where the bulge-forming layer 4 is not formed in the bulge-forming region 40).

In this way it is possible to improve adhesion between the core wire 3 and the coating layer 5, and to prevent peeling of the coating layer 5. No additional steps are necessary because fine surface irregularities are formed at the same time as the coating film is removed.

No specific restrictions are imposed on the method of removing the liquid material for the bulge-forming layer. Typical methods include grinding (with a grinder) and laser ablation (with a laser radiator). These methods give rise to the fine surface irregularities simultaneously with the removal of the coating film.

When applied to the coating film 41 of the liquid material for the bulge-forming layer, grinding makes round the edge 42 of the coating film 41. The round edge 42 help prevent bubbles from remaining in the part 43 where the coating film 41 has been removed, when the liquid material for the coating film is applied (mentioned later), and the part 43 is completely filled with the liquid material for the coating film. Thus the coating film 5 is relatively reliably protected from peeling.

(3) The coating film of the liquid material for the bulge-forming layer and the outer surface of the core wire 3 are coated (over the entire length of the core wire 3) with the liquid material for the coating layer 5 so that a coating film thereof is formed. Thus the film of the liquid material for the coating layer 5 covers the coating film of the liquid material for the bulge-forming layer and the outer surface of the core wire 3 over the entire length of the core wire 3. Then, the coating film of the liquid material for the coating layer 5 is dried.

(4) The outer surface of the coating film of the liquid material for the coating layer is coated with the liquid material for the outer layer 6 over the entire length of the core wire 3, so that a coating film thereof is formed. Thus the film of the liquid material for the outer layer 6 covers the coating film of the liquid material for the coating layer over the entire length of the core wire 3. Then, the coating film of the liquid material for the outer layer 6 is dried. This step (4) is not included in the first embodiment mentioned above.

(5) The coating films formed (laminated) on the core wire 3 are baked, so that the bulge-forming layer 4, the coating layer 5, and the outer layer 6 are formed.

Adequate conditions should be established according to the composition of the materials constituting the bulge-forming layer 4, the coating layer 5, and the outer layer 6. The baking temperature should preferably be about 330 to 600° C., more preferably about 380 to 500° C., and the baking duration should preferably be about 1 to 60 minutes, more preferably about 3 to 30 minutes.

After baking, the outer layer 6 (or the coating layer 5 in the first embodiment) is finished with hydrophilic or hydrophobic lubricating coating, if necessary. Thus there is obtained the guide wire 1 as desired.

Figure 6:
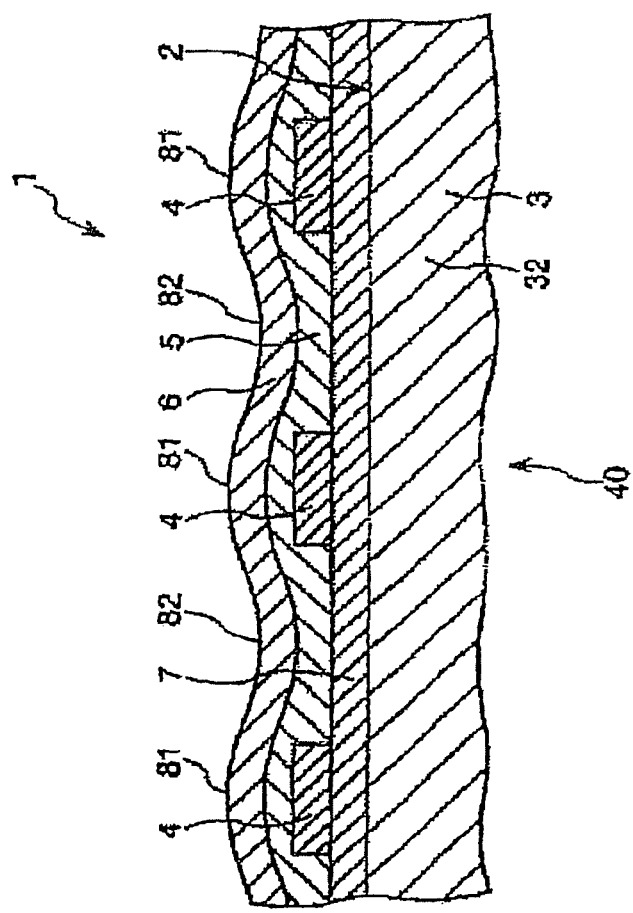
FIG. 6 is a partial longitudinal cross-sectional view of the part near the outer surface of the guide wire according to a fourth embodiment.
Figure 9:
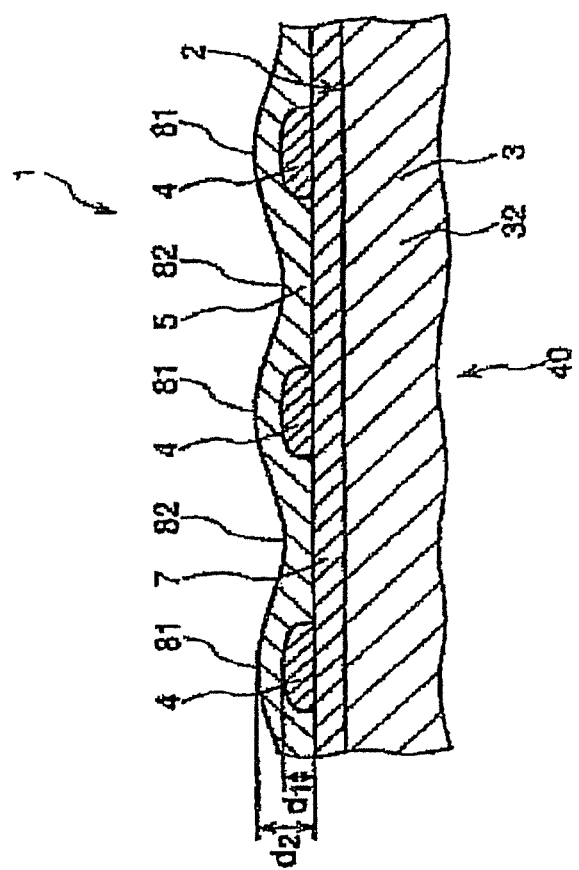
FIG. 9 is a partial longitudinal cross-sectional view of the part near the outer surface of the guide wire shown in FIG. 8.

Instead of above (1) and (2), the liquid material for the bulge-forming layer 4 can be applied to the bulge-forming region 40 on the outer surface of the core wire 3 or an undercoating layer 7 as shown in FIG. 6 or 9 so that the bulge-forming layer 4 has a desired pattern.

The guide wire 1 thus obtained produces the same effect as the guide wire 1 obtained in the first embodiment.

Incidentally, if the bulge-forming layer 4 is not required to function as a visible marker, the outer layer 6 may be opaque.

Figure 5:
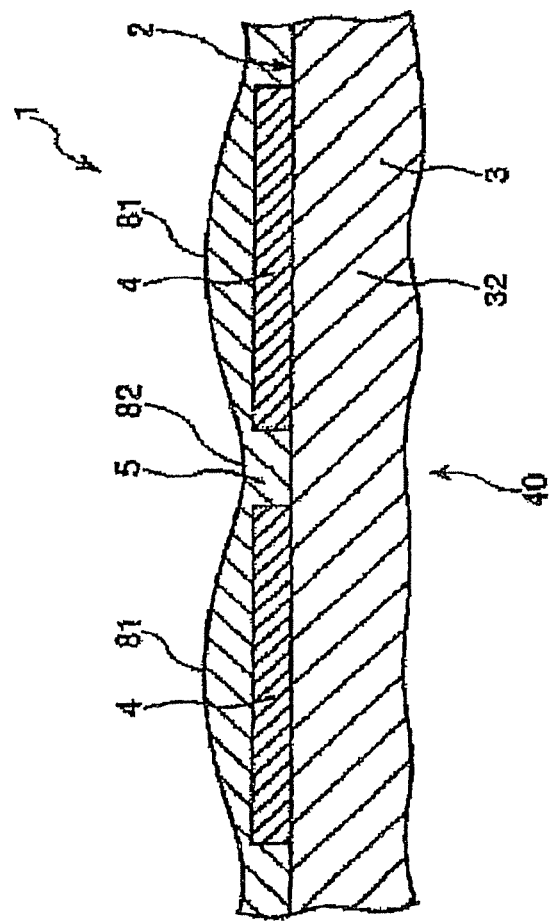
FIG. 5 is a partial longitudinal cross-sectional view of a part of the guide wire near the outer surface of the guide wire according to a third embodiment.

FIG. 5 is an illustration of the part of the guide wire near the outer surface of the guide wire according to a third embodiment.

The guide wire 1 according to the third embodiment is described below. The description primarily describes differences between this embodiment and the first embodiment. Features in this embodiment that are common to the first embodiment are identified with the same reference numerals and a detailed description of such features is not repeated.

In the guide wire 1 (shown in FIG. 5) according to the third embodiment, the coating layer 5 functions to reduce friction (sliding resistance) of the guide wire 1. The reduced friction contributes to the slidability and operability of the guide wire 1.

For the guide wire 1 to have reduced friction (sliding resistance), the coating layer 5 should be formed from a material which contains a resin (or a second resin) that reduces friction as mentioned below. As a result, the guide wire 1 exhibits a decrease in friction (sliding resistance) with the lumen of the catheter (which is used in combination with the guide wire 1) and also with the lumen of the endoscope, which leads to improved operability. The reduced sliding resistance helps prevent the guide wire 1 from kinking when the guide wire 1 is moved or rotated in the lumen of the catheter or in the lumen of the endoscope.

The bulge-forming layer 4 of the guide wire 1 is formed from a material containing a first resin, a second resin differing from the first resin and a pigment. And, the coating layer 5 is formed from a material containing the second resin. In other words, both the constituent material of the coating layer 5 and the constituent material of the bulge-forming layer 4 contain a common second resin. Thus, the bulge-forming layer 4 and the coating layer 5 firmly adhere (bond) to each other, and the coating layer 5 is protected from peeling when the guide wire 1 experiences bending and twisting repeatedly, even though the coating layer 5 contains the second resin which hardly adheres to the other member.

The bulge-forming layer 4 as a whole may contain the second resin in an amount of about 1 to 30 wt %, preferably about 3 to 20 wt %, so that good adhesion is achieved between the bulge-forming layer 4 and the coating layer 5.

The coating layer 5 as a whole may contain the second resin in an amount of about 1 to 30 wt %, preferably about 3 to 20 wt %, or the coating layer 5 may be formed solely from the second resin, so that good adhesion is achieved between the bulge-forming layer 4 and the coating layer 5, and the guide wire 1 has reduced friction (or sliding resistance).

The first resin is preferably any one of resins (1) and (2) listed below.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin includes fluororesins, such as polytetrafluoroethylene (PTFE), ethylene-tetrafluoroethylene copolymer (ETFE), and tetrafluoroethylene-perfluoroalkylvinyl ether copolymer (PFA). In the bulge-forming region 40, the area of the outer surface of the bulge-forming layer 4 is larger than that of the outer surface (immediately under the coating layer 5) of the core wire 3 where the bulge-forming layer 4 is not formed.

This structure results in a large area of contact between the bulge-forming layer 4 and the coating layer 5. Thus good adhesion is achieved between the bulge-forming layer 4 and the coating film 5. In this way the coating film 5 is reliably protected against peeling.

If S1 denotes the area of the outer surface of the bulge-forming layer 4 in the bulge-forming region 40 and S2 denotes the area of the outer surface (immediately under the coating layer 5) of the core wire 3 where the bulge-forming layer 4 is not formed in the bulge-forming region 40, the ratio of S1/S2 should preferably be about 1.5 to 10, more preferably about 3 to 8.

If the ratio of S1/S2 is larger than the upper limit given above (with the other conditions varied), there will be the possibility of the bulge-forming layer 4 decreasing in visibility. Also, if the ratio of S1/S2 is smaller than the lower limit given above, there will be the possibility of adhesion decreasing between the bulge-forming layer 4 and the coating layer 5.

The guide wire 1 thus obtained produces the same effect as the guide wire 1 obtained in the first embodiment mentioned above.

FIG. 6 illustrates the part near the outer surface of a guide wire according to a fourth embodiment.

The guide wire 1 according to the fourth embodiment is described below. The description primarily describes differences between this embodiment and the second embodiment. Features in this embodiment that are common to the second embodiment are identified with the same reference numerals and a detailed description of such features is not repeated.

As shown in FIG. 6, the guide wire 1 according to the fourth embodiment has the undercoating layer 7 which differs in color from the bulge-forming layer 4, and the bulge-forming layer 4 is formed partly on the outer surface of the undercoating layer 7.

The undercoating layer 7 covers the outer surface of the core wire 3 (or the member 2) at least in the bulge-forming region 40. According to this embodiment, the undercoating layer 7 covers the outer surface of the core wire 3 only in the bulge-forming region 40. This is not limitative; the undercoating layer 7 may cover the core wire 3 over its entire length.

The coating layer 5 firmly adheres to the undercoating layer 7 in that part of the bulge-forming region 40 at which the bulge-forming layer 4 is not formed.

The bulge-forming layer 4 of the guide wire 1 is formed from a material containing a first resin and a pigment, and the undercoating layer 7 is formed from a material containing a resin miscible with the first resin and a pigment different in color from the pigment in the bulge-forming layer 4. It should preferably be formed from a material containing the first resin and a pigment differing in color from the pigment of the bulge-forming layer 4. The color of the undercoating layer 7 depends mainly on the type and properties of the pigment contained therein, the type and properties (particularly color tone) of the resin contained therein, and the amount of the pigment contained therein. Any color can be obtained by adjustment of these factors.

Since the constituent material of the undercoating layer 7 and the constituent material of the bulge-forming layer 4 contain mutually miscible resins (particularly the first resin in common), the undercoating layer 7 and the bulge-forming layer 4 firmly adhere to each other. Therefore, the bulge-forming layer 4 protects itself from peeling even when the guide wire 1 experiences bending and twisting repeatedly.

The undercoating layer 7 as a whole may contain the resin (e.g., the first resin) miscible with the first resin in an amount of about 1 to 90 wt %, preferably about 5 to 50 wt %, so that good adhesion is achieved between the undercoating layer 7 and the bulge-forming layer 4.

The undercoating layer 7 as a whole may contain the pigment in an amount of about 10 to 99 wt %, preferably about 50 to 95 wt %, for a desired color, depending on the kind and properties of the pigment and the composition and characteristics of the resin material.

The pigment in the undercoating layer 7 may be uniformly dispersed. However, it may exist locally in the outer surface of the undercoating layer 7.

One or more than one kind of pigment may be used alone or in combination with one another (in the form of mixture). The one or more than one kind of pigment applies to both the undercoating layer 7 and the bulge-forming layer 4 having different colors relative to each other. The thickness of the undercoating layer 7 is not specifically restricted; it is usually about 1 to 20 μm, preferably about 2 to 10 μm.

The guide wire 1 thus obtained produces the same effect as the guide wire 1 obtained in the second embodiment mentioned above.

The advantage of the guide wire 1 is that the bulge-forming layer 4 and the undercoating layer 7 take on any desired color in response to the kind, properties, and amount of the pigment contained therein or the composition of the resin material contained therein. This offers a wide selection of colors for the visible marker and the undercoating layer 7, thereby giving a combination of the highly visible bulge-forming layer 4 and the undercoating layer 7. Thus the resulting guide wire 1 has a highly visible marker.

The fourth embodiment is also applicable to the first and third embodiments described above.

Figure 7:
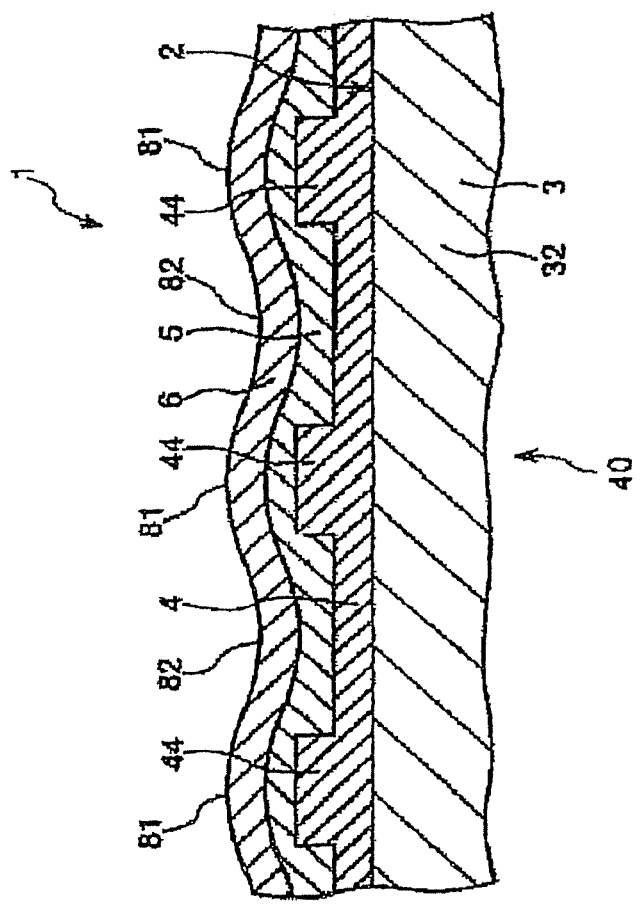
FIG. 7 is a partial longitudinal cross-sectional view of the part of the guide wire near the outer surface of the guide wire according to a fifth embodiment.

FIG. 7 illustrates a guide wire according to a further embodiment. More specifically, FIG. 7 shows the part near the outer surface of the guide wire according to a fifth embodiment.

The guide wire 1 according to the fifth embodiment is described below, primarily with reference to differences between this embodiment and the second embodiment. Features in this embodiment that are common to the second embodiment are identified with the same reference numerals and a detailed description of such features is not repeated.

In the guide wire 1 according to the fifth embodiment shown in FIG. 7, the bulge-forming layer 4 does not function as a visible marker, but rather functions as a means for the outer surface of the guide wire 1 to bulge (i.e., a means for forming the bulging part 81 and the recessed part 82).

The guide wire 1 has the bulge-forming layer 4 which is formed on the outer surface of the core wire 3 (or the member 2) in the bulge-forming region 40 so that the outer surface partly projects. In other words, the bulge-forming layer 4 has the partly projecting part 44 on the outer surface thereof.

The projecting part 44 is that part which corresponds to the bulge-forming layer 4 in the second embodiment mentioned above. On the outer surface of the outer layer 6 (or the outer surface of the guide wire 1), the part at which the projecting part 44 is formed (or the part corresponding to the projecting part of the bulge-forming layer 4) bulges relative to the part at which the projecting part 44 is not formed (or the part corresponding to the non-projecting part of the bulge-forming layer 4), so that the bulging part 81 and the recessed part 82 are formed.

The guide wire 1 thus obtained produces the same effect (except for the effect of visible marker) as the guide wire 1 obtained in the second embodiment mentioned above.

The fifth embodiment of the guide wire is also applicable to the first and third embodiments.

Figure 8:
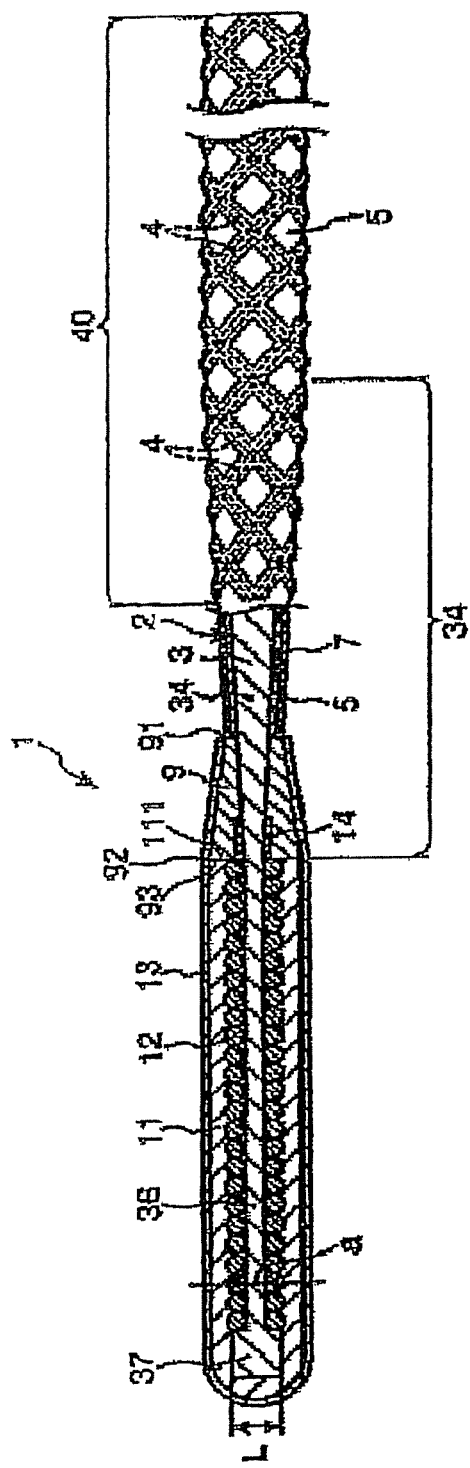
FIG. 8 is a partial longitudinal cross-sectional view of a sixth embodiment of the guide wire.

FIG. 8 shows a further embodiment of a guide wire. More specifically, FIG. 8 illustrates a sixth embodiment of the guide wire in longitudinal cross-sectional view, while FIG. 9 illustrates the part of the guide wire near the outer surface of the guide wire shown in FIG. 8. For the sake of convenience in description, the right and left sides in FIG. 8 are designated as the "base end" and the "forward end," respectively. In addition, to help facilitate an understanding, FIG. 8 schematically shows the guide wire with its length shortened and its thickness exaggerated. Therefore, the illustration is different from actual in the ratio of its thickness to length.

The guide wire 1 according to the fifth embodiment is described below, primarily with reference to differences between this embodiment and the first embodiment. Features in this embodiment that are common to the first embodiment are identified with the same reference numerals and a detailed description of such features is not repeated.

As shown in FIGS. 8 and 9, the guide wire 1 includes the member 2 (or the core wire 3), the spiral coil 12, the resin coating layer 11, the circular member 9 (step-filling member), the undercoating layer 7, the bulge-forming layer 4, the coating layer 5, and the hydrophilic lubricating layer 13.

The coil 12 is arranged around the forward end of the core wire 3 (or the member 2), i.e., around the small-diameter part 36 of the core wire 3. The coil 12 is a member which is formed by winding a thin wire around the small-diameter part 36 of the core wire 3 (or the member 2). In the case of the illustrated structure, the coil 12 is formed such that the adjacent wires are in contact with each other. In other words, the coil 12 is formed by tightly winding a thin wire around the core wire 3. In their natural state (without external force), the adjacent windings push against each other in the lengthwise direction of the member 2. Such compressive force in the natural state is not necessarily essential.

The coil 12 is wound such that it comes into contact with the outer surface of the small-diameter part 36 of the core wire 3. In other words, the inner surface of the coil 12 is in contact with the outer surface of the small-diameter part 36 of the core wire 3.

It is also possible for the coil 12 to be slipped on the small-diameter part 36 of the core wire 3, without contact between them. In other words, the thin wire of the coil 12 (inner surface of the coil 12) may be spaced away from the outer surface of the core wire 3. Also, the coil 12 may be wound such that the adjacent windings of the wire are not in contact with each other in the natural state without external force.

The coil 12 should preferably be formed from a metallic material, such as stainless steel, superelastic alloy, cobalt alloy, and noble metal (e.g., gold, platinum, and tungsten) and alloy thereof (e.g., platinum-iridium alloy). Noble metal opaque to X-rays is desirable because it permits the forward end of the guide wire 1 to be located when the guide wire 1 is inserted into a living body with the help of radioscopy. The coil 12 may be formed from different materials for its forward end and base end. For example, the forward end may be formed from a material opaque to X-rays and the base end may be formed from a material (such as stainless steel) relatively permeable to X-rays. The coil 12 may have an overall length of about 5 to 500 mm, which is not specifically restricted.

In this embodiment, the coil 12 is formed from a thin wire with a round cross section. However, the thin wire may have any cross section, such as ellipse, square, and rectangular.

The forward end of the core wire 3 is flat in shape (i.e., flat in cross-sectional shape). In other words, the core wire 3 has at its small-diameter part 36 the flat part 37 which is flat in shape. In the case of the illustrated structure, the flat part 37 is an approximately rectangular flat plate.

The width L of the flat part 37 (measured in the radial direction of the coil 12) is larger than the inside diameter a of the coil 12 (or the outside diameter D2 of the small-diameter part 36). And, the flat part 37 is located axially beyond, in the distal direction, the forward end of the coil 12. In other words, the coil 12 is arranged between the flat part 37 and the circular member 9 (mentioned later). The forward end of the coil 12 is engaged with a shoulder at the flat part 37, and the base end of the coil 12 is engaged with the forward end face 93 of the circular member 9.

This structure helps prevent the coil 12 from slipping off from the forward end of the core wire 3 (the member 2). Moreover, this structure reduces, and preferably eliminates, the need for material to fix the coil 12 to the core wire 3. Nevertheless, the coil 12 may be fixed to the core wire 3 by soldering or brazing or with an adhesive (boding agent), as a matter of course. The coil 12 may also be fixed by welding.

The flat part 37 may be formed by pressing. Specifically, pressing may be performed on the forward part of the core wire 3, with the small-diameter part 36 of the core wire 3 extended as much as the flat part 37. In this way the flat part 37 is formed at the forward end of the small-diameter part 36.

The guide wire 1 has the forward end of the core wire 3 (or the member 2), which includes the small-diameter part 36 and the flat part 37, and the resin coating layer 11 that covers the outer layer of the coil 12. The resin coating layer 11 firmly adheres to the flat part 37 of the core wire 3 and the outer surface of the coil 12.

The resin coating layer 11 is formed for various purposes, one of which it to ensure safe insertion of the guide wire 1 into a living body. For this reason, the resin coating layer 11 should preferably be formed from a flexible material (or soft and elastic material). In addition, it is desirable that the resin coating layer 11 be formed from a material which is more flexible than that for the bulge-forming layer 4, the coating layer 5, and the undercoating layer 7 (mentioned later).

Examples of the flexible material include polyolefins (such as polyethylene and polypropylene), polyvinyl chloride, polyester (such as PET and PBT), polyamide, polyimide, polyurethane, polystyrene, silicone resin, thermoplastic elastomers (such as polyurethane elastomer, polyester elastomer, and polyamide elastomer), rubbers (such as latex gum and silicone rubber), and composite materials thereof.

The resin coating film 11 formed from any one of the foregoing thermoplastic elastomers or rubbery materials makes the forward end of the guide wire 1 more flexible. Hence it contributes to safety without the possibility of damaging the internal wall when the guide wire 1 is inserted into a living body.

The resin coating film 11 should preferably contain fine particles (filler) dispersed therein which are opaque to X-rays (functioning as a contrast medium), so that it permits the forward end of the guide wire 1 to be located at the time of insertion into a living body with the help of radioscopy. The foregoing particles may be formed any material opaque to X-rays, such as gold, platinum, tungsten, and alloy thereof (such as platinum-iridium alloy).

The thickness of the resin coating film 11 is not specifically restricted; it depends on the object, material, and fabricating method. A preferred thickness is about 20 to 500 μm, more preferably about 30 to 300 μm. With an excessively small thickness, the resin coating film 11 may not fully produce its effect. With an excessively large thickness, the resin coating film 11 may adversely affect the physical properties of the member 2 (or the guide wire 1). The resin coating layer 11 may be a laminate composed of two or more layers.

The base end of the resin coating layer 11 is a certain distance away from the forward end of the coating layer 5 and the undercoating layer 7 (mentioned later). There is the circular member 9 which fills the gap of the step between the base end of the resin coating layer 11 and the member 2. The circular member 9 tightly encloses the outer surface of the tapered part 34 of the core wire 3. The forward end 92 of the circular member 9 is at the base end of the resin coating layer 11 and the base end 91 of the circular member 9 is at the forward end of the undercoating layer 7 and the coating layer 5.

The outside diameter of the base end of the resin coating layer 11 is larger than that of the member 2 at the base end of the resin coating layer 11, and the above-mentioned gap between the steps is due to the difference in the outside diameters.

The outside diameter of the forward end 92 of the circular member 9 is approximately equal to that of the base end of the resin coating layer 11, so that the forward end 93 of the circular member 9 closely adheres to the base end face 111 of the resin coating layer 11. In this case, the resin coating layer 11 does not extend toward the base end beyond the forward end 92 of the circular member 9 and does not overlap the circular member 9. In other words, there is a stepless continuous surface between the forward end 92 of the circular member 9 and the base end of the resin coating layer 11.

The outside diameter of the circular member 9 gradually decreases in going from the forward end toward the base end, so that the outside diameter of the base end 91 of the circular member 9 is smaller than the outside diameter of the forward end 92. And, the outside diameter of the base end 91 of the circular member 9 is approximately equal to the outside diameter of the coating layer 5 at the base end 91 of the circular member 9. In other words, there is a stepless continuous surface between the coating layer 5 and the base end 91 of the circular member 9. The outside diameter 91 of the circular member 9 is smaller than the outside diameter of the main body 32 of the core wire 3. The base end 91 of the circular member 9 is positioned closer to the forward end than the base end 341 of the tapered part (See FIG. 1). The circular member 9 is 0.5 to 15 mm long.

The inside diameter of the base end 91 of the circular member 9 is larger than the inside diameter of the forward end 92. This is because the circular member 9 is positioned at the tapered part 34 of the core wire 3. It is also possible that the inside diameter of the base end 91 is identical with that of the forward end 92.

The circular member 9 prevents the base end of the resin coating layer 11 from being caught by the forward end of the catheter (to be used in combination with the guide wire 1) or by the medical instrument such as the stand of the endoscope. In this way it is possible to prevent the resin coating layer 11 from peeling and also to prevent the guide wire 1 from decreasing in slidability due to the step mentioned above.

The hardness of the circular member 9 should be higher than that of the resin coating layer 11. In this way it is possible to prevent the circular member 9 from being caught by the forward end of the catheter (to be used in combination with the guide wire 1) or by the medical instrument such as the stand of the endoscope.

The circular member 9 may have its forward end face 93 and/or the inner surface roughened. Surface irregularities on the forward end face 93 contribute to adhesion to the resin coating layer 11, and surface irregularities on the inner surface contribute to adhesion to the core wire 3 and the fixing material 14 (mentioned later).

The circular member 9 may be formed from any material, such as resins and metals, without specific restrictions. The constituent material may be identical with or different from that for the resin coating layer 11.

However, the circular member 9 should preferably be formed from a metallic material or a hard resin material, with the former being particularly desirable.

The hard resin material for the circular member 9 includes polycarbonate, polyamide (nylon), polyethylene terephthalate, polyacetal, and polyphenylene sulfide.

The metallic material for the circular member 9 includes stainless steel, titanium, titanium alloy, Ni—Ti alloy, aluminum, gold, and platinum. Noble metals (such as gold and platinum) and alloys thereof are preferable because they function as a good contrast medium for X-rays.

In the case where the circular member 9 is formed from a metallic material, its outer surface may be covered with a coating layer (no shown). This coating layer may be formed from any material such as resins, ceramics, and metals, which are not specifically restricted. Insulating materials are particularly desirable.

The circular member 9 is fixed to the core wire 3 (or the member 2) by the fixing material 14 arranged on the outer surface of the tapered part 34 of the core wire 3.

The fixing material 14 may be solder or adhesive. An insulating adhesive is particularly desirable.

The method for fixing the circular member 9 is not limited to one employing the fixing material.

In the illustrated structure, the whole body of the circular member 9 is positioned at the tapered part 34. However, an instance is permissible in which only a portion of the circular member 9 is positioned at the tapered part 34.

The circular member 9 functions to relieve difference in stiffness (flexural and torsional stiffness) between the base end side and forward end side (beyond the circular member 9) of the member 2. The circular member 9 prevents stiffness from abruptly increasing at the base end of the resin coating layer 11, thereby helping to avoid kinking at the base end of the resin coating layer 11.

The guide wire 1 should preferably have at least the outer surface of its forward end coated with the hydrophilic lubricating layer 13 formed from a hydrophilic material. In this embodiment, the hydrophilic lubricating layer 13 covers the outer surface of the guide wire 1 (or the outer surface from the base end 91 to the forward end of the circular member 9 of the guide wire 1) in the region from the forward end of the guide wire 1 to the base end 91 of the circular member 9 (the forward end of the undercoating layer 7 and the coating layer 5), or the outer surface of the resin layer 11 and the circular member 9. The hydrophilic material produces lubricity upon getting wet, thereby reducing the friction (sliding resistance) and improving the slidability of the guide wire 1. This contributes to the operability of the guide wire 1.

The hydrophilic material includes cellulosic high-molecular materials, polyethylene oxide high-molecular materials, maleic anhydride high-molecular materials (such as methyl vinyl ether-maleic anhydride copolymer), acrylamide high-molecular materials (such as polyacrylamide, polyglycidyl methacrylate-dimethyl acrylamide (PGMA-DMAA) block copolymer), water-soluble nylon, polyvinyl alcohol, and polyvinyl pyrrolidone.

These hydrophilic compounds usually exhibit lubricity upon moisture (water) absorption, thereby reducing frictional resistance (sliding resistance) due to contact with the lumen of the catheter (to be used in combination with the guide wire 1) and the lumen of the endoscope. Such lubricity improves the slidability and operability of the guide wire 1 in the lumen of the catheter and the lumen of the endoscope.

The guide wire 1 has the undercoating layer 7 which differs in color from the bulge-forming layer 4. The bulge-forming layer 4 is formed partly on the outer surface of the undercoating layer 7. As shown in FIG. 8, the bulge-forming layer 4 is formed in a grid-like pattern. And, the bulge-forming region 40 extends from the base end of the core wire 3 to the midway of the tapered part 34 (the position closer to the base end side than the circular member 9). However, it may extend over the entire length of the core wire 3.

The undercoating layer 7 covers the outer surface of the core wire 3 (or the member 2) in at least the bulge-forming region 40. In this embodiment, the undercoating layer 7 extends from the base end of the core wire 3 to the base end 91 of the circular member 9. And, the coating layer 5 adheres to the undercoating layer 7 at the part where the bulge-forming layer 4 is not formed in the bulge-forming region 40.

Incidentally, the undercoating layer 7 may also cover the outer surface of the core wire 3 only in the bulge-forming region 40 or may entirely cover the core wire 3 (along the overall length).

The undercoating layer 7 is formed from a material containing a resin and a pigment differing in color from the pigment for the bulge-forming layer 4. The color of the undercoating layer 7 depends mainly on the type and properties of the pigment contained therein, the type and properties (particularly color tone) of the resin contained therein, and the amount of the pigment contained therein. Any color can be obtained by adjustment of these factors.

The constituent material of the undercoating layer 7 may contain at least one of the resins which is preferably miscible with the resin contained in the constituent material of the bulge-forming layer 4, and it is desirable to use common resins. In other words, it is desirable that the constituent material of the undercoating layer 7 and the constituent material of the bulge-forming layer 4 contain mutually miscible resins, preferably common resins. This results in firm adhesion between the bulge-forming layer 4 and the undercoating layer 7. Thus, the bulge-forming layer 4 protects itself from peeling even when the guide wire 1 experiences bending and twisting repeatedly.

The undercoating layer 7 as a whole may contain the miscible resin (particularly common resins) mentioned above in an amount of about 1 to 90 wt %, preferably about 5 to 50 wt %, so that good adhesion is achieved between the undercoating layer 7 and the bulge-forming layer 4.

The undercoating layer 7 and the coating layer 5 should preferably be formed from materials containing mutually miscible resin, desirably common resins, so that good adhesion is achieved between the coating layer 5 and the undercoating layer 7 in the region where the bulge-forming layer 4 is not formed. Thus the coating layer 5 protects itself from peeling even when the guide wire 1 experiences bending and twisting repeatedly. The content of pigment in the undercoating layer 7 as a whole depends on the type and properties of the pigment and the composition and characteristics of the resin; it is usually about 10 to 99 wt %, preferably about 50 to 95 wt %.

The pigment in the undercoating layer 7 should be uniformly dispersed. However, it may exist locally in the outer surface of the undercoating layer 7.

One or more than one kind of pigment may be used alone or in combination with one another (in the form of mixture). The one or more than one kind of pigment applies to both the undercoating layer 7 and the bulge-forming layer 4 having different relative colors.

The thickness of the undercoating layer 7 is not specifically restricted; it is usually about 1 to 20 μm, preferably about 2 to 10 μm, and more preferably about 3 to 8 μm.

The thickness d1 (maximum thickness) of the bulge-forming layer 4 is also not specifically restricted; it is usually about 1 to 30 μm, preferably about 2 to 10 μm, more preferably 3 to 8 μm.

The total thickness of the coating layer 5 and the bulge-forming layer 4 is not specifically restricted. The total value d2 (maximum value) of the coating film 5 and the bulge-forming layer 4 in the bulging part 81 may be 50 μm or smaller. It should preferably be about 2 to 40 μm, more preferably about 4 to 30 μm, and most desirably about 15 to 25 μm.

The guide wire 1 according to this embodiment produces the same effect as the guide wire 1 according to the first embodiment mentioned above.

The advantage of the guide wire 1 is that the bulge-forming layer 4 and the undercoating layer 7 take on any desired color in response to the kind, properties, and amount of the pigment contained therein or the composition of the resin material contained therein. This offers a wide selection of colors for the visible marker and the undercoating layer 7, thereby giving a combination of the highly visible bulge-forming layer 4 and the undercoating layer 7 regardless of the color of the core wire 3 (the member 2). Thus the resulting guide wire 1 has a highly visible marker.

The sixth embodiment is also applicable to the second and third embodiments mentioned above.

Figure 10:
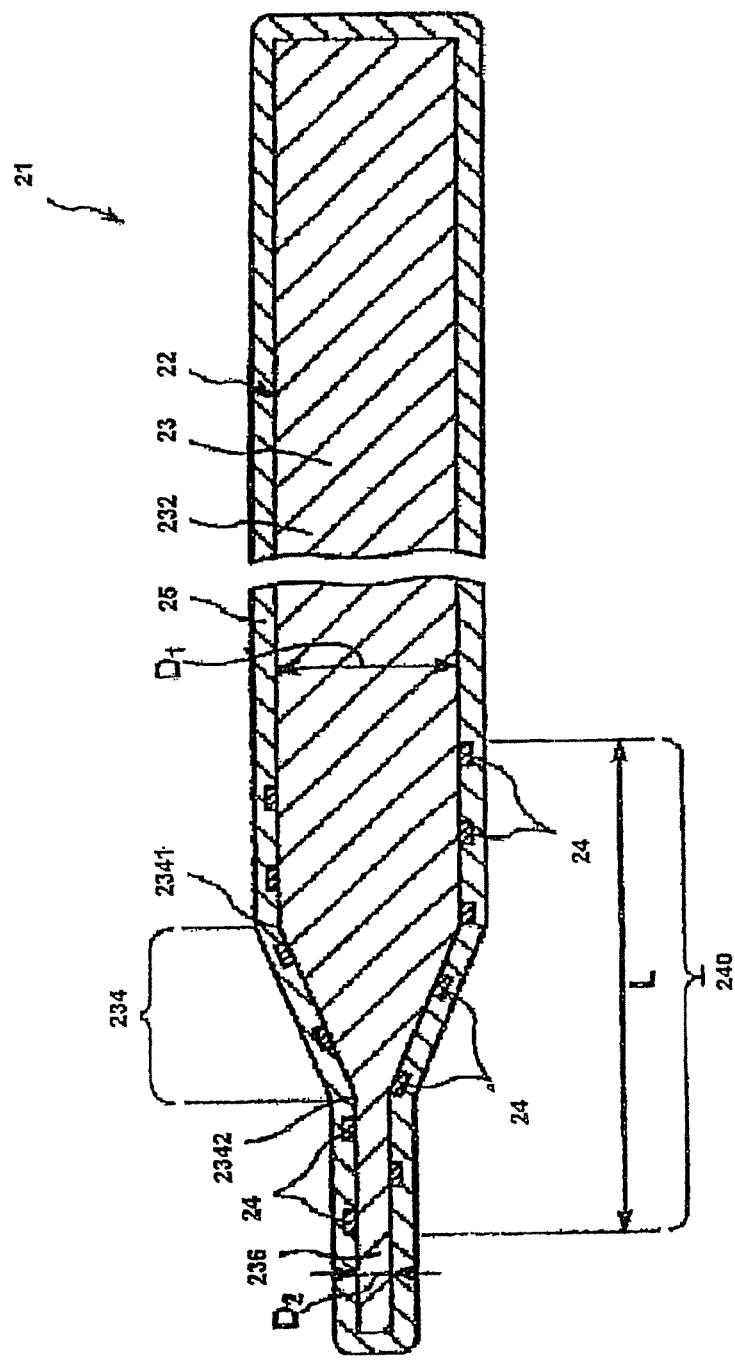
FIG. 10 is a longitudinal cross-sectional view of a seventh embodiment of the guide wire.

FIG. 10 is a longitudinal cross-sectional view of a seventh embodiment of the guide wire. As shown in FIG. 10, the guide wire 21 includes a member 22, a marker-forming layer 24, and a coating layer 25. The member 22 is a flexible core wire 23. The marker-forming layer 24 differs in color from the member 22 (or the core wire 23). The coating layer 25 has such transparency (light transmission) as to make the marker-forming layer 24 visible.

According to this embodiment, the member 22 is a single continuous core wire 23 and has a round cross section. However, the member 22 may be composed of two or more different or identical core wires joined together by welding or brazing. It may also have any additional structure.

The guide wire 21 is not specifically restricted in its overall length. A preferred overall length is about 200 to 5,000 mm. Also, it is not specifically restricted in outside diameter. A preferred outside diameter is about 0.2 to 1.2 mm.

The core wire 23 extends over the entire length of the guide wire 21. It includes a main part 232 (which corresponds to the main body of the guide wire 21), a tapered part 234 (which is close to the forward end), and a thin part 236 (at the forward end). The main part 232 has a constant outside diameter (inclusive of nearly constant). The tapered part 234 gradually decreases in outside diameter toward the forward end. The thin part 236 also has a constant outside diameter (inclusive of nearly constant).

The tapered part 234 makes the core wire 23 gradually (continuously) increase in flexibility from the boundary (or the base end 2341 of the tapered part) between the main part 232 and the tapered part 234 toward the forward end. This adds flexibility to the guide wire 21, thereby making it easier and safer to insert the guide wire 21 into a living body.

The thin part 236 that extends in an elongated manner toward the forward end from the tapered part 234 is more flexible than the rest of the guide wire. The main part 232 of the core wire 23 has an outside diameter D1 (measured at the base end 2341 of the tapered part), which is not specifically restricted but should preferably be about 0.3 to 1.0 mm, more preferably about 0.4 to 0.7 mm.

The thin part 236 of the core wire 23 has an outside diameter D2 (measured at the forward end 2342 of the tapered part), which is not specifically restricted but should preferably be about 0.05 to 0.3 mm, more preferably about 0.1 to 0.2 mm. The outside diameter of the thin part 236 may be constant or may gradually decrease in going toward the forward end.

The length of the tapered part 234 may vary depending on the use and kind of the guide wire without specific restrictions. It should preferably be about 10 to 300 mm, more preferably about 30 to 250 mm.

The length of the thin part 236 is not specifically restricted. It should preferably be about 0 to 100 mm, more preferably about 10 to 50 mm.

The tapered part 234 may decrease in outside diameter at a constant rate or a varying rate along the lengthwise direction of the core wire 23 (the member 22). There may be two or more of the tapered part 234.

The core wire 23 should preferably have minute surface irregularities. This is true particularly for that part of the outer surface (immediately under the coating layer 25) where the marker-forming layer 24 in the marker-forming region 240 (mentioned later) is not yet formed. The surface irregularities improve adhesion between the core wire 23 and the coating layer 25, thereby preventing the coating layer 25 from peeling off.

The core wire 23 may be made of metallic materials, such as stainless steel, Ni—Ti alloy, Ni—Al alloy, Cu—Zn alloy, and other superelastic alloys, or resin materials having a comparatively high stiffness. They may be used alone or in combination with one another.

The guide wire 21 according to the present invention is not specifically restricted in its application. It may be used, for example, to guide a catheter to a desired position (such as a cavity in a living body) through the lumen of an endoscope. (It will be referred to as "transendoscopic guide wire.") The embodiment mentioned below is concerned typically with the case in which the guide wire 21 is used as a transendoscopic guide wire.

The transendoscopic guide wire has a visible marker on its outer surface, so that the marker is visible through the endoscope. In this embodiment, the marker-forming layer 24 functions as the visible marker.

The guide wire 21 has the marker-forming region 240 in which the marker-forming layer 24 is formed. On the outer layer of the core wire 23 (or the member 22) in the marker-forming region 240 is a portion of the marker-forming layer 24. In other words, the marker-forming layer 24 is formed tightly on the outer surface of the core wire 23 at prescribed intervals, and the coating layer 25 between individual marker-forming layers 24 is formed tightly on the core wire 23. The marker-forming layer 24 differs in color from the outer surface of the core wire 23 (or the member 22), so that it functions as the visible marker.

The marker-forming region 240 may extend entirely or partly (along the overall length) in the lengthwise direction of the core wire 23. In this embodiment, the marker-forming region 240 is formed in the forward section of the core wire 23 including the tapered part 234.

The marker-forming region 240 may have a length L in the lengthwise direction which is not specifically restricted. The length L should preferably be about 10 to 50 cm, more preferably about 20 to 40 cm.

The marker-forming layer 24 may be formed from a material containing a resin and a pigment. The color of the marker-forming layer 24 depends mainly on the kind, amount, and properties of the pigment contained therein and also on the composition and properties (especially color) of the resin material contained therein. Any color can be produced by their adequate combination.

The color of the marker-forming layer 24 is important for the operator to observe the movement of the guide wire 21 through the endoscope. An adequate color should be selected in view of the color of the core wire 23 (or the member 22) underneath.

To cite an example, the core wire 23 or its oxide coating film may have a silver white color (metallic color) or a grayish or black color, and the marker-forming layer 24 may have a reddish or yellowish color. In this case there is a large difference in brightness between them, which gives rise to a high contract. Thus the marker-forming layer 24 is highly visible, which is desirable. Another case in which they have complementary colors is also desirable because of the high visibility of the marker-forming layer 24. A high contrast is obtained when a dark color such as black (or dark colors such as charcoal gray, dark brown, navy blue, and violet) is combined with a light color (such as yellow, yellowish green, and orange), or when blue is combined with red, orange, or pink. A high contrast is also obtained by combination of the same colors differing in shade, such as dark blue with light blue and reddish-brown with pink.

The constituent material of the marker-forming layer 24 may contain any resin without specific restrictions. However, any one of resins (1) and (2) listed below is preferable.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, polyethersulfone, and fluororesin, such as polytetrafluoroethylene (PTFE) and ethylene-tetrafluoroethylene copolymer (ETFE). They may be used alone or in combination with one another.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The marker-forming layer 24 as a whole should contain pigment in an amount of about 10 to 99 wt %, preferably about 50 to 95 wt %, to produce desired colors. An adequate amount depends on the type and properties of the pigment and the composition and properties of the resin material. The marker-forming layer 24 should preferably contain pigment uniformly distributed therein, although uneven distribution in its outer surface is permissible.

Pigments may be used alone or in combination with one another in the form of mixture.

The marker-forming layer 24 is not specifically restricted in shape (pattern) and dimensions. However, it should preferably have a thickness of about 1 to 20 µm, more preferably about 2 to 10 µm, so that the guide wire 21 can be made thin.

As shown in the figure, the marker-forming layer 24 takes on a spiral pattern. The spiral (or circular) pattern has a width of about 1 to 10 mm and extends over about 10 to 50 cm in the lengthwise direction of the guide wire 21, at intervals of about 1 to 10 mm.

The shape of the marker-forming layer 24 is not restricted to spiral or circular. It can also be in the form of a straight line, wavy pattern, polka dots, check pattern, and mesh pattern. The shape of the marker-forming layer 24 can also include numerals, letters, symbols, and graduations, which are visible. Two or more different patterns may be combined with each other (for example, a spiral pattern and a circular pattern placed on top of the other) for better visibility.

The pigment may be either inorganic pigments or organic pigments, with the former being preferable because of their good heat resistance. Inorganic pigments include carbon black, mica, titanium dioxide, nickel-titanium yellow, prussian blue, milori blue, cobalt blue, ultramarine, and viridian blue.

The coating layer 25 has such transparency as to make the marker-forming layer 24 visible. It covers the marker-forming layer 24 and the core wire 23 (or the member 22) in at least the marker-forming region 240. In this embodiment, the coating layer 25 covers not only the marker-forming region 240 but also the marker-forming layer 24 and the entire length of the core wire 23. The coating layer 25 is formed from a resin-containing material. As shown in FIG. 10, the coating layer 25 where the marker-forming layer 24 is located has a substantially constant outer diameter.

The constituent material of the coating layer 25 may contain any resin which is not specifically restricted. At least one of the resins should be the one which is miscible with the resin contained in the constituent material of the marker-forming layer 24. In other words, mutually miscible resins should be contained in the constituent material for the coating layer 25 and the constituent material for the marker-forming layer 24. This helps ensure relatively firm adhesion between the marker-forming layer 24 and the coating layer 25, thereby helping to prevent the coating layer 25 from peeling off even when the guide wire 21 experiences repeated bending and twisting.

"Miscibility" means that the two components dissolve well each other thermodynamically. In other words, they do not separate from each other after curing.

Mutually miscible resins may be the same ones or different ones. Combination of different resins is that of polyamideimide and polyimide, polyetherimide and polyimide, polyamideimide and polyetherimide, or polysulfone and polyethersulfone, which have common groups, such as imide and sulfone.

The content of the mutually miscible resins in the marker-forming layer 24 should preferably be about 1 to 90 wt %, more preferably about 5 to 50 wt %, based on the total weight of the marker-forming layer 24, for good adhesion between the marker-forming layer 24 and the coating layer 25.

The content of the mutually miscible resins in the coating layer 25 should preferably be about 1 to 50 wt %, more preferably about 3 to 35 wt %, based on the total weight of the coating layer 25, for good adhesion between the marker-forming layer 24 and the coating layer 25.

The coating layer 25 is not specifically restricted in thickness. It should preferably have a thickness of about 1 to 20 µm, more preferably about 2 to 10 µm.

The total thickness of the coating layer 25 and the marker-forming layer 24 is not specifically restricted; it should be equal to or smaller than 50 µm, preferably about 2 to 40 µm, more preferably about 4 to 20 µm.

The foregoing thickness is necessary for the guide wire 21 to have a small diameter. This object is not achieved with the conventional visible marker, which is formed by covering the core wire with a heat-shrinkable tube (as thick as about 100 µm) having a spiral or parallel stripy pattern. In this embodiment, the marker-forming layer 24 and the coating layer 25 having the foregoing thickness can be formed easily and certainly by using the structure (mentioned above) and the production method (mentioned later).

The method for producing the guide wire 21 is not specifically discussed here, but will be mentioned later together with the method for producing the guide wire 21 according to the eighth embodiment.

As mentioned above, the guide wire 21 according to the seventh embodiment has a small diameter, and the marker-forming layer 24 thereon has any desired color owing to adequate selection of pigment and resin material (for composition and amount). The marker-forming layer 24 allows a wide selection of colors for any color of the core wire 23 (or the member 22). Therefore, the resulting guide wire 21 has an easily visible marker.

Since the coating layer 25 and the marker-forming layer 24 are formed from mutually miscible resins, they firmly adhere to each other and the coating layer 25 remains without peeling off even when the guide wire 21 experiences bending and twisting repeatedly.

According to this embodiment, the member 22 is formed from the core wire 23, and the marker-forming layer 24 and the coating layer 25 are formed directly on the outer surface of the core wire 23. However, the guide wire is not limited to this structure. For example, the core wire 23 may have on its outer surface one or more layers and may further have the marker-forming layer 24 and the coating layer 25 on such layers. In this case, the member 22 has one or more layers on the outer surface of the core wire 23 such that they cover the outer surface partly or entirely.

Figure 11:
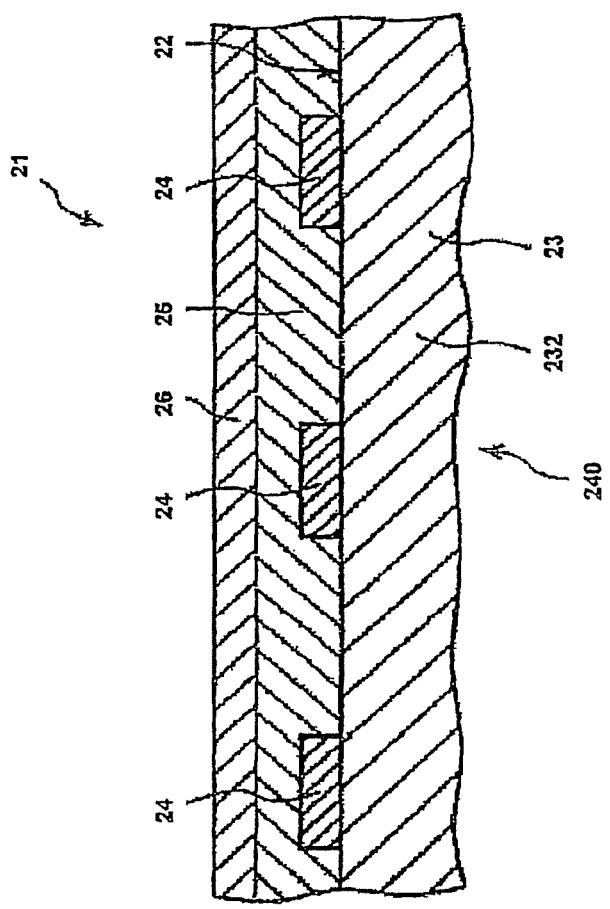
FIG. 11 is a partial longitudinal cross-sectional view of the marker-forming region in an eighth embodiment of the guide wire.
Figure 12:
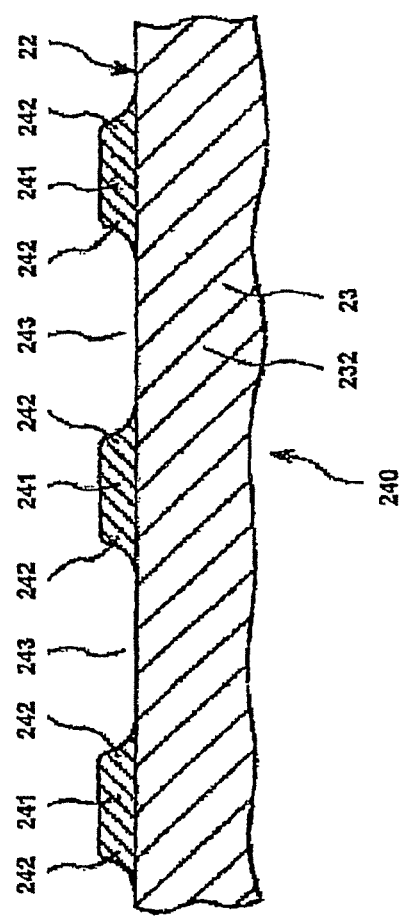
FIG. 12 is a partial longitudinal cross-sectional view of the marker-forming region, illustrating the method for producing the guide wire shown in FIG. 11.

FIG. 11 is a partial longitudinal cross-sectional view of the marker-forming region in an eighth embodiment of the guide wire. FIG. 12 shows the marker-forming region of the guide wire. FIG. 12 schematically illustrates an aspects of the method for producing the guide wire shown in FIG. 11.

The guide wire 21 according to the eighth embodiment is described below. The description primarily describes differences between this embodiment and the seventh embodiment. Features in this embodiment that are common to the seventh embodiment are identified with the same reference numerals and a detailed description of such features is not repeated.

As shown in FIG. 11, the guide wire 21 according to the eighth embodiment has an outer layer 26 which covers the coating layer 25 and has such transparency as to make the marker-forming layer 24 visible. The outer layer 26 may cover the coating layer 25 partly or entirely (throughout the entire length).

The outer layer 26 may be formed for various purposes. One purpose is to reduce the friction (sliding resistance) or improve the slidability of the guide wire 21, which contributes to the operability of the guide wire 21.

For the guide wire 21 to have reduced friction (sliding resistance), the outer layer 26 should be formed from a material which contains a resin (or a second resin) that reduces friction as mentioned below. As a result, the guide wire 21 exhibits a decrease in friction (sliding resistance) relative to the lumen of the catheter (which is used in combination with the guide wire 21) and also with respect to the lumen of the endoscope, which leads to improved operability. The reduced sliding resistance helps prevent the guide wire 21 from kinking when the guide wire 21 is moved or rotated in the lumen of the catheter or in the lumen of the endoscope.

As shown in FIG. 11, the outer layer 26 where the marker-forming layer 24 is located has a substantially constant outer diameter.

The thickness of the outer layer 26 is not specifically restricted; it is usually about 1 to 15 µm, preferably about 2 to 10 µm. An excessively large thickness might physically affect the guide wire 21 and is disadvantageous for the guide wire 21 to have a small diameter.

The marker-forming layer 24 of the guide wire 21 is formed from a material containing a first resin and a pigment. And, the coating layer 25 is formed from a material containing a resin miscible with the first resin and a second resin differing from the miscible resin. Preferably, it should be formed from a material containing the first resin and a second resin differing from the first resin. Also, the outer layer 26 is formed from a material containing the second resin.

Thus, the coating layer 25 functions as an adhesive layer (or adhesive) to bond the marker-forming layer 24 and the outer layer 26 together. Therefore, even though the second resin contained in the outer layer 26 is one which hardly adheres to other members, the outer layer 26 protects itself from peeling. In other words, since the coating layer 25 and the marker-forming layer 24 are formed from materials containing mutually miscible resins (or the first resin which is common to them), the marker-forming layer 24 and the coating layer 25 firmly adhere (bond) to each other, and, since the outer layer 26 and the coating layer 25 are formed from the second resin which is common to them, the coating layer 25 and the outer layer 26 firmly adhere to each other. Thus, the coating layer 25 and the outer layer 26 protect themselves from peeling even when the guide wire 21 experiences bending and twisting repeatedly.

The marker-forming layer 24 as a whole may contain the first resin in an amount of about 1 to 90 wt %, preferably about 5 to 50 wt %, so that good adhesion is achieved between the marker-forming layer 24 and the coating layer 25.

The coating layer 25 as a whole may contain a resin (e.g., the first resin) which is miscible with the first resin in the coating layer 25 in an amount of about 1 to 50 wt %, preferably about 3 to 35 wt %, so that good adhesion is achieved between the marker-forming layer 24 and the coating layer 25.

The coating layer 25 as a whole may contain the second resin in an amount equal to or more than 50 wt %, preferably about 50 to 99 wt %, more preferably about 65 to 97 wt %, so that good adhesion is achieved between the coating layer 25 and the outer layer 26.

The outer layer 26 as a whole may contain the second resin in an amount of about 1 to 30 wt %, preferably about 3 to 20 wt %, or the outer layer 26 should be formed solely from the second resin, so that good adhesion is achieved between the coating layer 25 and the outer layer 26 and the guide wire 21 has reduced friction (or sliding resistance).

The first resin is not specifically restricted. However, it should preferably be any one of resins (1) and (2) listed below.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin to make the guide wire 21 decrease in friction (or sliding resistance) includes fluororesins, such as polytetrafluoroethylene (PTFE), ethylene-tetrafluoroethylene copolymer (ETFE), and tetrafluoroethylene-perfluoroalkylvinyl ether copolymer (PFA).

The following is a description of the method for producing the guide wire 21 according to this eighth embodiment, it being understood that this method is also applicable to the fabrication of the seventh embodiment of the guide wire except for aspects of the method pertaining to the outer layer 26.

(1) The first step is to prepare a liquid material for the marker-forming layer 24 (composed of the constituent of the marker-forming layer 24 and a solvent), a liquid material for the coating layer 25 (composed of the constituent of the coating layer 25 and a solvent), and a liquid material for the outer layer 26 (composed of the constituent of the outer layer 26 and a solvent).

Next, the liquid material for the marker-forming layer 24 is applied to the marker-forming region 240 on the outer surface of the core wire 23 (or the member 22), so that a coating film is formed entirely on the marker-forming region 240. The coating film is dried.

Incidentally, the marker-forming layer 24, the coating layer 25, and the outer layer 26 should have the thickness and other dimensions as mentioned above, which are not repeated here.

(2) The coating film formed from the liquid material for the marker-forming layer 24 is partly removed so that the marker-forming layer 24 has a desired pattern.

The coating film should preferably be removed in such a way as to form fine surface irregularities in that part of the outer surface of the core wire 23 from which the coating film is removed (or the surface directly under the coating layer 25 at the part where the marker-forming layer 24 is not formed in the marker-forming region 240).

In this way it is possible to improve adhesion between the core wire 23 and the coating layer 25 and to prevent peeling of the coating layer 25. No additional steps are necessary because fine surface irregularities are formed at the same time as the coating film is removed.

In the case of a core wire made of Ni—Ti alloy, for example, the surface is covered with oxide film and the oxide film peels off as the coating film is removed, so that the silver white color of Ni—Ti alloy appears. This color produces a high contrast if an adequate color is used for the marker-forming layer 24.

No specific restrictions are imposed on the method of removing the liquid material for the marker-forming layer. Typical methods include grinding (with a grinder) and laser ablation (with a laser radiator). These methods give rise to the fine surface irregularities simultaneously with the removal of the coating film.

When applied to the coating film 241 of the liquid material for the marker-forming layer, grinding makes round the edge 242 of the coating film 241, as shown in FIG. 12. The round edge 242 prevents bubbles from remaining in the part 243 where the coating film 41 has been removed, when the liquid material for the coating film is applied (mentioned later), and the part 243 is completely filled with the liquid material for the coating film. Thus the coating film 25 is surely protected from peeling.

(3) The coating film of the liquid material for the marker-forming layer 24 and the outer surface of the core wire 23 are coated (over the entire length of the core wire 23) with the liquid material for the coating layer 25 so that a coating film thereof is formed. Thus the film of the liquid material for the coating layer 25 covers the coating film of the liquid material for the marker-forming layer and the outer surface of the core wire 23 over the entire length of the core wire 23. Then, the coating film of the liquid material for the coating layer is dried.

The coating film of the liquid material for the coating layer 25 is not necessarily required to cover the entire length of the core wire 23 so long as it covers the marker-forming region 240.

(4) The outer surface of the coating film of the liquid material for the coating layer is coated with the liquid material for the outer layer 26 over the entire length of the core wire 23, so that a coating film thereof is formed. Thus the film of the liquid material for the outer layer 26 covers the coating film of the liquid material for the coating layer over the entire length of the core wire 23. Then, the coating film of the liquid material for the outer layer is dried. This step (4) is not included in the seventh embodiment mentioned above.

(5) The coating films formed (laminated) on the core wire 23 are baked, so that the marker-forming layer 24, the coating layer 25, and the outer layer 26 are formed.

Adequate conditions should be established according to the composition of the materials constituting the marker-forming layer 24, the coating layer 25, and the outer layer 26. The baking temperature should preferably be about 330 to 600° C., more preferably about 380 to 500° C., and the baking duration should preferably be about 1 to 60 minutes, more preferably about 3 to 30 minutes.

After baking, the outer layer 26 is finished with hydrophilic or hydrophobic lubricating coating, if necessary. Thus there is obtained the guide wire 21 as desired.

The guide wire 21 thus obtained produces the same effect as the guide wire 21 obtained in the seventh embodiment.

Figure 13:
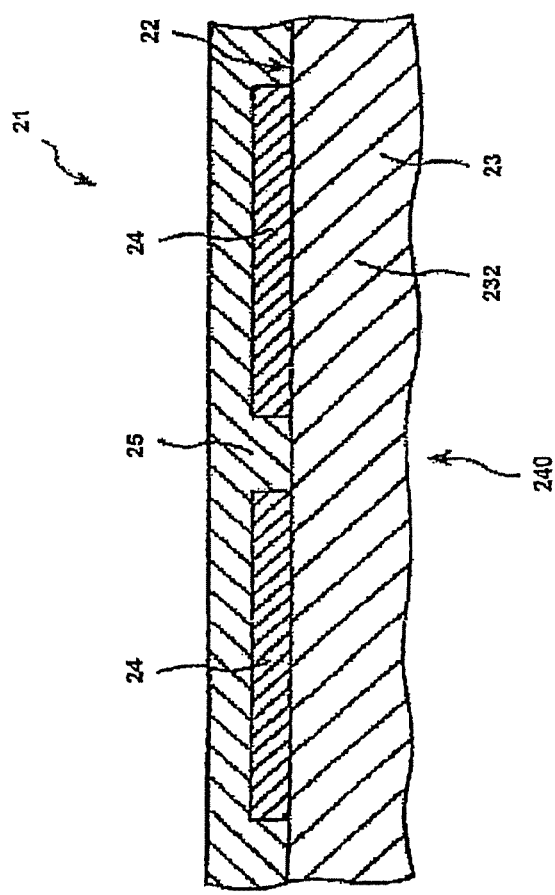
FIG. 13 is a partial longitudinal cross-sectional view of the marker-forming region in a ninth embodiment of the guide wire.

FIG. 13 illustrates the marker-forming region in a ninth embodiment of the guide wire.

The guide wire 21 according to the ninth embodiment is described below. The description primarily describes differences between this embodiment and the seventh embodiment. Features in this embodiment that are common to the seventh embodiment are identified with the same reference numerals and a detailed description of such features is not repeated.

In the ninth embodiment of the guide wire 21 shown in FIG. 13, the coating layer 25 functions to reduce friction (sliding resistance) of the guide wire 21. The reduced friction contributes to the slidability and operability of the guide wire 21.

For the guide wire 21 to have reduced friction (sliding resistance), the coating layer 25 should be formed from a material which contains a resin (or a second resin) that reduces friction as mentioned below. As a result, the guide wire 21 exhibits decreased friction (sliding resistance) with the lumen of the catheter (which is used in combination with the guide wire 21) and also with the lumen of the endoscope, which leads to improved operability. The reduced sliding resistance contributes to preventing the guide wire 21 from kinking when the guide wire 21 is moved or rotated in the lumen of the catheter or in the lumen of the endoscope.

The marker-forming layer 24 of the guide wire 21 is formed from a material containing a first resin, a second resin differing from the first resin, and a pigment. And, the coating layer 25 is formed from a material containing the second resin. In other words, both the constituent material of the coating layer 25 and the constituent material of the marker-forming layer 24 contain the common second resin. Thus, the marker-forming layer 24 and the coating layer 25 firmly adhere (bond) to each other, and the coating layer 25 protects itself from peeling when the guide wire 21 experiences bending and twisting repeatedly, even though the coating layer 25 contains the second resin which hardly adheres to the other member.

The marker-forming layer 24 as a whole may contain the second resin in an amount of about 1 to 30 wt %, preferably about 3 to 20 wt %, so that good adhesion is achieved between the marker-forming layer 24 and the coating layer 25.

The coating layer 25 as a whole may contain the second resin in an amount of about 1 to 30 wt %, preferably about 3 to 20 wt %, or the coating layer 25 may be formed solely from the second resin, so that good adhesion is achieved between the marker-forming layer 24 and the coating layer 25 and the guide wire 21 has reduced friction (or sliding resistance).

The first resin is not specifically restricted. However, it should preferably be any one of resins (1) and (2) listed below.

(1) Heat-Resistant Resins which have a Melting Point of 200° C. or Higher, Preferably about 200 to 300° C.

Examples of the heat-resistant resins include polysulfone, polyimide, polyether-ether ketone, polyarylene ketone, polyphenylenesulfide, polyarylenesulfide, polyamideimide, polyetherimide, polyimidesulfone, polyarylsulfone, polyarylethersulfone, polyester, and polyethersulfone.

(2) Thermosetting Resins.

Examples of the thermosetting resins include epoxy resin, phenolic resin, unsaturated polyester resin, polyimide resin, silicone resin, and polyurethane resin. They may be used alone or in combination with one another.

The second resin includes fluororesins, such as polytetrafluoroethylene (PTFE), ethylene-tetrafluoroethylene copolymer (ETFE), and tetrafluoroethylene-perfluoroalkylvinyl ether copolymer (PFA). In the marker-forming region 240, the area of the outer surface of the marker-forming layer 24 is larger than that of the outer surface (immediately under the coating layer 25) of the core wire 23 where the marker-forming layer 24 is not formed.

This structure results in a large area of contact between the marker-forming layer 24 and the coating layer 25. Thus good adhesion is achieved between the marker-forming layer 24 and the coating layer 25. In this way the coating layer 25 surely protects itself from peeling.

If S1 denotes the area of the outer surface of the marker-forming layer 24 in the marker-forming region 240 and S2 denotes the area of the outer surface (immediately under the coating layer 25) of the core wire 23 where the marker-forming layer 24 is not formed in the marker-forming region 240, then the ratio of S1/S2 should preferably be about 1.5 to 10, more preferably about 3 to 8.

If the ratio of S1/S2 is larger than the upper limit given above (with the other conditions varied), there will be the possibility of the marker-forming layer 24 decreasing in visibility. Also, if the ratio of S1/S2 is smaller than the lower limit given above, there will be the possibility of adhesion decreasing between the marker-forming layer 24 and the coating layer 25.

The guide wire 21 thus obtained produces the same effect as the guide wire 21 obtained in the seventh embodiment mentioned above.

Figure 14:
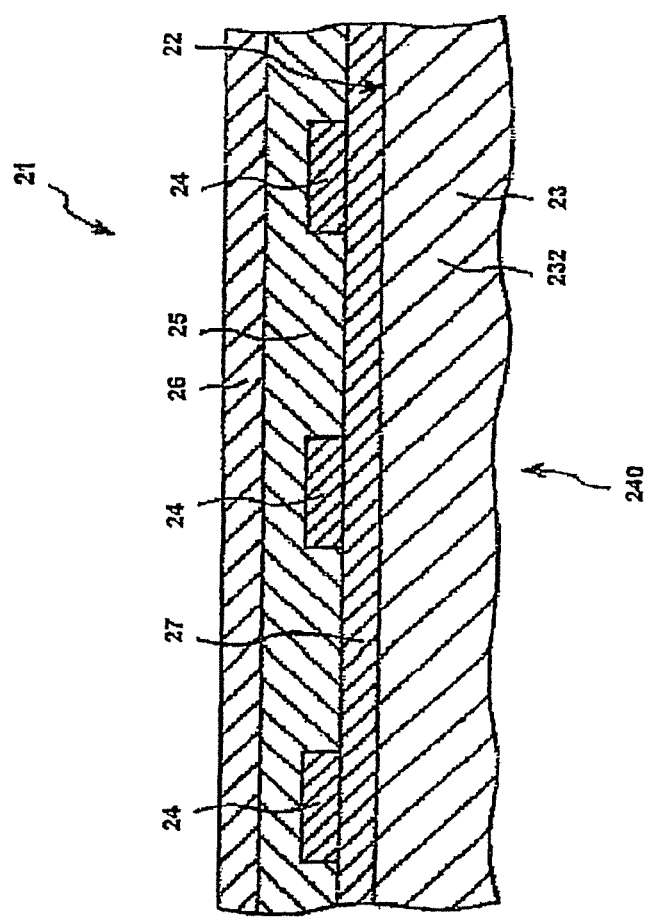
FIG. 14 is a partial longitudinal cross-sectional view of the marker-forming region in a tenth embodiment of the guide wire.

FIG. 14 is a longitudinal cross-sectional view of the marker-forming region in a tenth embodiment of the guide wire disclosed here.

The guide wire 21 according to the tenth embodiment is described below, primarily with reference to differences between this embodiment and the eight embodiment of the guide wire. Features in this embodiment that are common to the eighth embodiment are identified with the same reference numerals and a detailed description of such features is not repeated.

As shown in FIG. 14, the guide wire 21 according to the tenth embodiment includes the undercoating layer 27 which differs in color from the marker-forming layer 24, and the marker-forming layer 24 is formed partly on the outer surface of the undercoating layer 27.

The undercoating layer 27 covers the outer surface of the core wire 23 (or the member 22) at least in the marker-forming region 240. According to this embodiment, the undercoating layer 27 covers the outer surface of the core wire 23 only in the marker-forming region 240. This is not limitative as the undercoating layer 27 may cover the core wire 23 over its entire length.

The marker-forming layer 24 of the guide wire 21 is formed from a material containing a first resin and a pigment, and the undercoating layer 27 is formed from a material containing a resin miscible with the first resin and a pigment different in color from the pigment in the marker-forming layer 24. It should preferably be formed from a material containing the first resin and a pigment differing in color from the pigment of the marker-forming layer 24. The color of the undercoating layer 27 depends mainly on the type and properties of the pigment contained therein, the type and properties (particularly color tone) of the resin contained therein, and the amount of the pigment contained therein. Any color can be obtained by adjustment of these factors.

Since the constituent material of the undercoating layer 27 and the constituent material of the marker-forming layer 24 contain mutually miscible resins (particularly the first resin in common), the undercoating layer 27 and the marker-forming layer 24 firmly adhere to each other. Therefore, the marker-forming layer 24 protects itself from peeling even when the guide wire 21 experiences bending and twisting repeatedly.

The undercoating layer 27 as a whole may contain the resin (e.g., the first resin) miscible with the first resin in an amount of about 1 to 90 wt %, preferably about 5 to 50 wt %, so that good adhesion is achieved between the undercoating layer 27 and the marker-forming layer 24.

The undercoating layer 27 as a whole may contain the pigment in an amount of about 10 to 99 wt %, preferably about 50 to 95 wt %, for a desired color, depending on the kind and properties of the pigment and the composition and characteristics of the resin material.

The pigment in the undercoating layer 27 should be uniformly dispersed. However, it may exist locally in the outer surface of the undercoating layer 27.

One or more than one kind of pigment may be used alone or in combination with one another (in the form of mixture).

The thickness of the undercoating layer 27 is not specifically restricted; it is usually about 1 to 20 μm, preferably about 2 to 10 μm.

The guide wire 21 thus obtained produces the same effect as the guide wire 21 obtained in the eighth embodiment mentioned above.

The advantage of the guide wire 21 is that the marker-forming layer 24 and the undercoating layer 27 take on any desired color in response to the kind, properties, and amount of the pigment contained therein or the composition of the resin material contained therein. This offers a wide selection of colors for the visible marker and the undercoating layer 27, thereby giving a combination of the highly visible marker-forming layer 24 and the undercoating layer 27 regardless of the color of the core wire 23 (the member 22). Thus the resulting guide wire 21 has a highly visible marker.

The aspects of the tenth embodiment of the guide wire are also applicable to the seventh and ninth embodiments.

Figure 15:
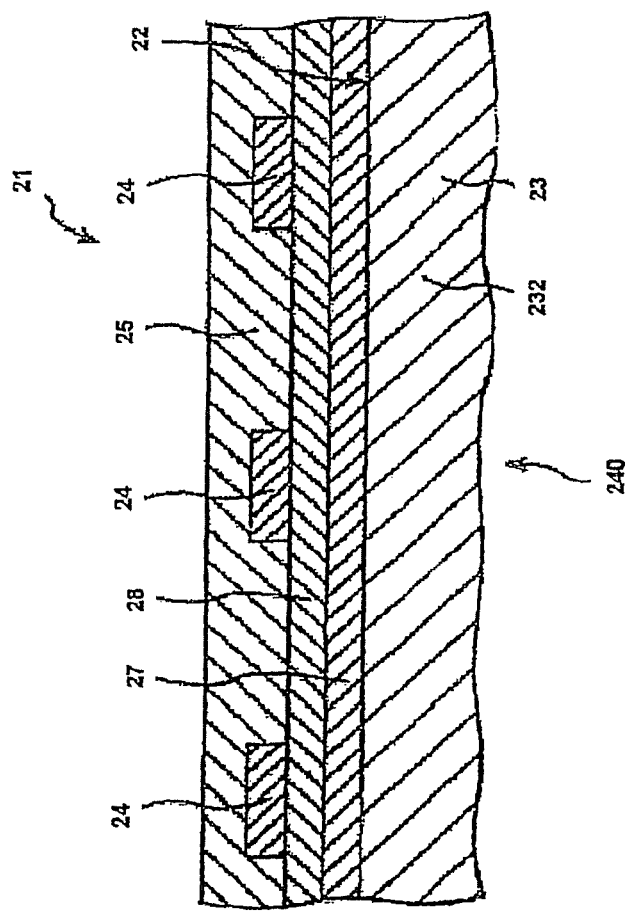
FIG. 15 is a partial longitudinal cross-sectional view of the marker-forming region in an eleventh embodiment of the guide wire.

FIG. 15 illustrates the marker-forming region according to an eleventh embodiment of the guide wire.

The guide wire 21 according to the eleventh embodiment is described below. The description primarily describes differences between this embodiment and the seventh embodiment. Features in this embodiment that are common to the seventh embodiment are identified with the same reference numerals and a detailed description of such features is not repeated.

As shown in FIG. 15, the guide wire 21 according to the eleventh embodiment has the undercoating layer 27 and an intermediate layer 28, and the marker-forming layer 24 is formed partly on the outer surface of the intermediate layer 28 (or above the intermediate layer 28).

The undercoating layer 27 covers the outer surface of the core wire 23 (or the guide member 22) at least in the marker-forming region 240. In this embodiment, the undercoating layer 27 covers the outer surface of the core wire 23 only in the marker-forming region 240. However, modifications are possible in which the undercoating layer 27 covers the core wire 23 entirely (over the entire length thereof), or has a color different from that of the marker-forming layer 24.

Also, the intermediate layer 28 covers the outer surface of the undercoating layer 27. In this embodiment, the intermediate layer 28 is formed only in the marker-forming region 240. However, modifications are possible in which the intermediate layer 28 covers the entire length of the core wire 23, or has a color different from that of the marker-forming layer 24.

The coating layer 25 that reduces friction (or sliding resistance) makes the guide wire 21 easy to operate.

For the guide wire 21 to have improved operability with reduced friction (or sliding resistance), it is desirable to make the coating layer 25 from a material containing a resin (mentioned below) which reduces friction. In this way, the guide wire 21 exhibits decreased friction (sliding resistance) with the lumen of the catheter (which is used in combination with the guide wire 21) and also with the lumen of the endoscope, which leads to improved operability. The reduced sliding resistance prevents the guide wire 21 from kinking when the guide wire 21 is moved or rotated in the lumen of the catheter or in the lumen of the endoscope.

The marker-forming layer 24 is formed from a material containing a resin and a pigment. The composition of the material is exemplified by Compositions (1) to (3) below.

(Composition 1)

A material contains a second resin (mentioned later, which differs from the first resin), and a pigment. The second resin should preferably be any of fluororesins mentioned in the eighth embodiment.

The marker-forming layer 24 as a whole should contain the second resin in an amount of about 1 to 90 wt %, preferably about 5 to 50 wt %, so that good adhesion is achieved between the marker-forming layer 24 and the coating layer 25 or between the marker-forming layer 24 and the intermediate layer 28.

(Composition 2)

A material contains a second resin (mentioned later, which differs from the first resin), a third resin (which differs from the second resin), and a pigment.

The second and third resins should be mutually different fluororesins used in the eighth embodiment. For example, a combination of PTFE and PFA is preferable. The first and third resins should also be mutually different.

The marker-forming layer 24 as a whole should contain the second resin in an amount of about 1 to 81 wt %, preferably about 5 to 45 wt %, so that good adhesion is achieved between the marker-forming layer 24 and the coating layer 25 or between the marker-forming layer 24 and the intermediate layer 28.

Also, the marker-forming layer 24 as a whole should contain the third resin in an amount of about 1 to 81 wt %, preferably about 5 to 45 wt %, so that good adhesion is achieved between the marker-forming layer 24 and the coating layer 25.

(Composition 3)

A material contains a second resin (mentioned later, which differs from the first resin), a fourth resin (which differs from the second resin), and a pigment.

The second resin should be a fluororesin used in the eighth embodiment. The fourth resin should be a heat-resistant resin used in the eighth embodiment, which has a melting point of 200° C. or higher, preferably about 200 to 300° C. The fourth resin should be a thermosetting resin used in the eighth embodiment. The second and fourth resins should be mutually different. For example, a combination of PFA and polyimide is preferable. The first and fourth resins may be mutually different or the same.

The marker-forming layer 24 as a whole may contain the second resin in an amount of about 1 to 30 wt %, preferably about 3 to 20 wt %, so that good adhesion is achieved between the marker-forming layer 24 and the coating layer 25 or between the marker-forming layer 24 and the intermediate layer 28.

The marker-forming layer 24 as a whole may contain the fourth resin in an amount of about 1 to 60 wt %, preferably about 3 to 30 wt %, so that good adhesion is achieved between the marker-forming layer 24 and the intermediate layer 28.

The coating layer 25 is formed from a material containing a resin (mentioned later) differing from the first resin. It should preferably be formed from a material containing mutually different two resins.

In the case where the marker-forming layer 24 is formed from a material having the composition 2 mentioned above, the coating layer 25 is formed from a material containing mutually different two resins. One of them is miscible with the second resin mentioned above, preferably the second resin itself mentioned above. The other of them is miscible with the third resin mentioned above, preferably the third resin itself mentioned above. Thus, the guide wire 21 has reduced friction (or sliding resistance) and good adhesion (bonding) is achieved between the marker-forming layer 24 and the coating layer 25.

The coating layer 25 as a whole may contain one of the resins mentioned above in an amount of about 1 to 30 wt %, preferably about 3 to 20 wt %, and the coating layer 25 as a whole should contain the other of the resins mentioned above in an amount of about 80 to 97 wt %, so that good adhesion is achieved between the coating layer 25 and the marker-forming layer 24 as wells as the intermediate layer 28 and the guide wire 21 has reduced friction (or sliding resistance).

In the case where the marker-forming layer 24 is formed from a material having the composition 1 mentioned above or the composition 3 mentioned above, the coating layer 25 should preferably be formed from a material containing mutually different two resins. However, it may also be formed from a material containing only one resin.

In the case where the coating layer 25 is formed from a material containing only one resin, the resin should be miscible with the second resin mentioned above, or preferably the second resin itself, so that the guide wire 21 has reduced friction (or sliding resistance) and good adhesion (bonding) is achieved between the marker-forming layer 24 and the coating layer 25.

In the case where the coating layer 25 is formed from a material containing mutually different two resins, one of them should be miscible with the second resin mentioned above (preferably the second resin itself) and the other of them should be the fluororesin used in the second embodiment mentioned above, so that the guide wire 21 has reduced friction (or sliding resistance) and good adhesion (bonding) is achieved between the marker-forming layer 24 and the coating layer 25.

The content of each of the resins mentioned above is as mentioned above.

The intermediate layer 28 is formed from a material containing a first resin, a resin which is different from the first resin and miscible with the second resin mentioned above, and a pigment. Preferably, it is formed from a material containing a first resin, a second resin differing from the first resin, and a pigment. The pigment in this case should preferably be one which differs in color from that in the marker-forming layer 24.

The first resin may be a heat resistant resin having a melting point of 200° C. or higher, preferably about 200 to 300° C., like the one mentioned in the eighth embodiment. The first resin should be a thermosetting resin like the one mentioned in the eighth embodiment.

The color of the intermediate layer 28 depends mainly on the type and properties of the pigment contained therein, the composition and properties (particularly color tone) of the resin contained therein, and the amount of the pigment contained therein. Any color can be obtained by adjustment of these factors.

The intermediate layer 28 as a whole may contain the first resin in an amount of about 1 to 60 wt %, preferably about 3 to 30 wt %, so that good adhesion is achieved between the intermediate layer 28 and the undercoating layer 27.

Also, the intermediate layer 28 as a whole may contain the resin (e.g., the second resin) miscible with the second resin contained therein in an amount of about 1 to 30 wt %, preferably about 3 to 20 wt %, so that the marker-forming layer 24 firmly adheres to the intermediate layer 28 and the coating layer 25.

Also, the intermediate layer 28 as a whole may contain the pigment in an amount of about 10 to 98 wt %, preferably about 50 to 94 wt %, depending on the type and properties of the pigment therein and the composition of the resin therein, so that it takes on a desired color. The pigment in the intermediate layer 28 may be uniformly dispersed. However, it may exist locally in the outer surface of the intermediate layer 28.

The pigments may be used alone or in combination with one another.

The intermediate layer 28 may not contain the pigment. The thickness of the intermediate layer 28 is not specifically restricted; it should be about 1 to 20 μm, preferably about 2 to 10 μm.

The undercoating layer 27 is formed from a material containing a resin miscible with the first resin and a pigment, preferably from a material containing the first resin and a pigment. The pigment should preferably differ in color from the one contained in the marker-forming layer 24.

The color of the undercoating layer 27 depends mainly on the type and properties of the pigment contained therein, the composition and properties (particularly color tone) of the resin contained therein, and the amount of the pigment contained therein. Any color can be obtained by adjustment of these factors.

The undercoating layer 27 as a whole may contain the resin (e.g., the first resin) miscible with the first resin in an amount of about 1 to 90 wt %, preferably about 5 to 50 wt %, so that good adhesion is achieved between the undercoating layer 27 and the intermediate layer 28.

The content of the pigment in the undercoating layer 27 depends on the type and properties of the pigment and the composition and properties of the resin. For a desirable color, it is about 10 to 99 wt %, preferably about 50 to 95 wt %.

The pigment in the undercoating layer 27 may be uniformly dispersed. However, it may exist locally in the outer surface of the undercoating layer 27.

The pigments may be used alone or in combination with one another.

The undercoating layer 27 may not contain the pigment. The thickness of the undercoating layer 27 is not specifically restricted; it should be about 1 to 20 μm, preferably about 2 to 10 μm.

As mentioned above, the constituent material of the coating layer 25 and the constituent material of the marker-forming layer 24 contain mutually miscible resin (particularly the second resin in common), so that good adhesion is achieved between the marker-forming layer 24 and the coating layer 25.

Also, the constituent material of the marker-forming layer 24 and the constituent material of the intermediate layer 28 contain mutually miscible resin (particularly the second resin in common), so that good adhesion is achieved between the marker-forming layer 24 and the intermediate layer 28. Further, good adhesion is achieved between the coating layer 25 and the intermediate layer 28.

Also, the constituent material of the intermediate layer 28 and the constituent material of the undercoating layer 27 contain mutually miscible resin (particularly the first resin in common), so that good adhesion is achieved between the intermediate layer 28 and the undercoating layer 27.

This structure helps to prevent the individual layers from peeling off even when the guide wire 21 experiences bending and twisting repeatedly. The guide wire 21 thus obtained produces the same effect as the guide wire 21 obtained in the first embodiment mentioned above.

The advantage of the guide wire 21 is that the marker-forming layer 24, the undercoating layer 27, and the intermediate layer 28 take on any desired color in response to the kind, properties, and amount of the pigment contained therein or the composition of the resin material contained therein. This offers a wide selection of colors for the visible marker and the undercoating layer 7, thereby giving a combination of the highly visible marker-forming layer 24, the undercoating layer 27, and the intermediate layer 28 regardless of the color of the core wire 23 (or the member 22). Thus the resulting guide wire 21 has a highly visible marker.

The guide wire 21 may additionally have an outer layer.

The guide wire should preferably be one which produces X-ray contrast images, so that it can be located in the living body. This can be achieved by adding a contrast medium (or a filler containing a contrast medium) to a desired position in the specific layer. The contrast medium is not specifically restricted so long as it gives X-ray contrast images; though it is preferably selected from metal powder or metal oxide powder.

Also, the guide wire according to the present invention is not limited to one used in the context of inserting it into the lumen of an endoscope.

FIGS. 16-21 illustrate another embodiment of the guide wire having some similarities to the embodiment of the guide wire shown in FIG. 8. In the following description, for purposes of convenience, the right side in FIGS. 16, 17, 20 and 21 (and FIGS. 22 and 23, also) is referred to as "proximal," and the left side as "distal." In addition, as mentioned above, the guide wire in FIG. 16 is depicted as being shortened in the longitudinal direction and exaggerated in the radial direction, so that the ratio between the longitudinal size and the radial size in the figure is different from the ratio in practice.

Figure 16:
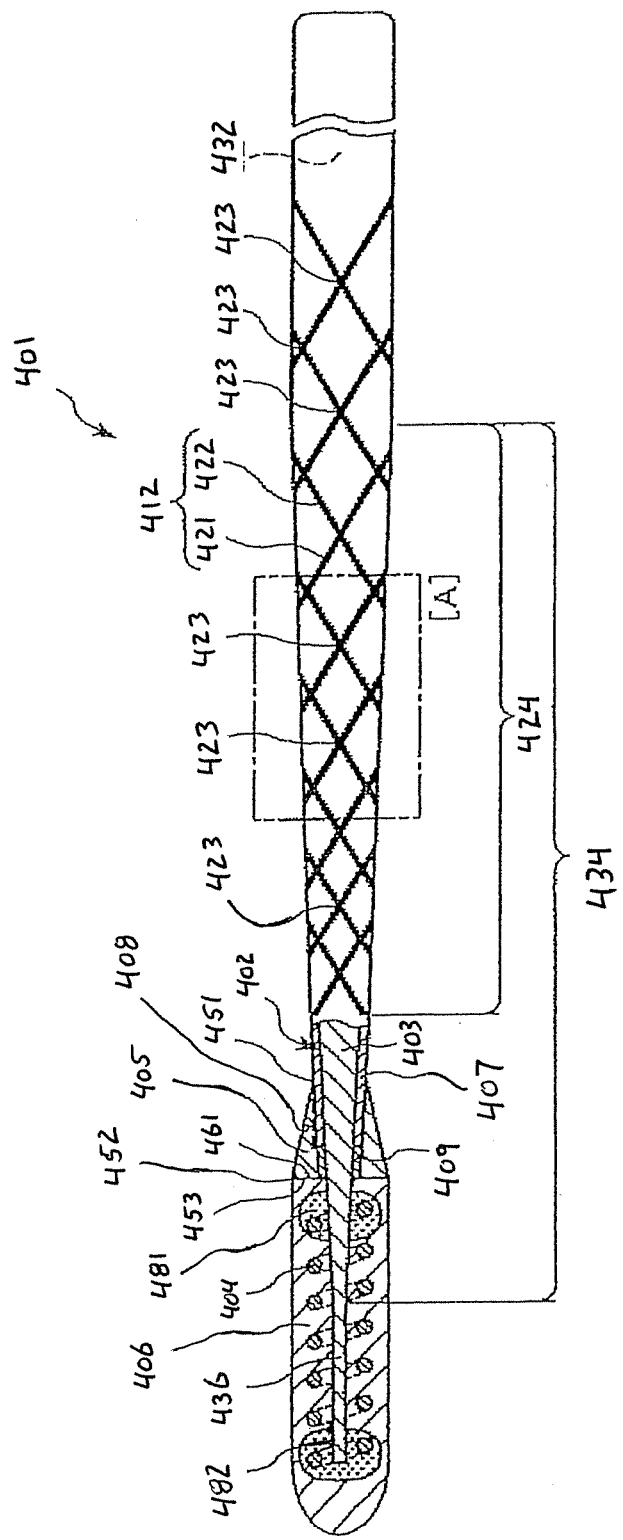
FIG. 16 is a partial longitudinal cross-sectional view of a twelfth embodiment of the guide wire disclosed here.

The guide wire 401 shown in FIG. 16 is a catheter guide wire to be used while inserted in the lumen of a catheter (inclusive of an endoscope). The guide wire 401 has a wire body or wire member 402 composed of a flexible or pliable core wire 403, a helical coil 404, a resin coating layer 406, an annular member 405, and a marker 412.

In this embodiment, the wire body 402 is comprised of a single, elongate, continuous core wire 403. The core wire 403 is circular in cross-sectional shape. However, the core wire 403 is not limited in this regard. For example, the core wire 403 may be formed by joining a plurality of core wires of the same or different materials by, for example, welding or soldering. As described in more detail below, the core wire in this embodiment is comprised of a body portion 432, a tapered portion 434, and a small-diameter portion 436. Where the core wire 403 is formed by joining two core wires, for example, the joint may be located in any of the body portion 432, the tapered portion 434, and the small-diameter portion 436.

The overall length of the guide wire 401 is not particularly limited, though is preferably about 200 to 5000 mm. In addition, the outer diameter of the guide wire 401 is not particularly limited, but is preferably about 0.2 to 1.2 mm.

The core wire 403 extends over substantially the entire length of the guide wire 401. The core wire 403 has the body portion 432 corresponding to the body portion of the guide wire 401, the tapered portion 434 located on the distal side of the body portion 432, and the small-diameter portion 436 located on the distal side of the tapered portion 434. The body portion 432 is substantially constant in outer diameter, the tapered portion 434 has an outer diameter gradually decreasing in the distal direction, and the small-diameter portion 436 is substantially constant in outer diameter.

Since the core wire 403 is provided with the tapered portion 434, the flexibility of the core wire 403 is gradually increased in the distal direction from the vicinity of the boundary part between the body portion 432 and the tapered portion 434. As a result, the flexibility of the guide wire 401 is increased, so that steerability and safety at the time of inserting the guide wire 401 into a living body are enhanced.

The marker 412 is provided on the tapered portion 434 of the guide wire, extending from an intermediate part toward the proximal side as shown in FIG. 16. This helps ensure that the marker 412 is disposed on a comparatively highly flexible portion, or an easily deformable portion, of the guide wire 401. Consequently, when this portion is curved, the degree of curving can be checked.

In addition, since the small-diameter portion 436 is provided on the distal side of the tapered portion 434, the distalmost flexible portion can be relatively long, resulting in the distalmost portion being more flexible.

At least a part of the small-diameter portion 436 of the core wire 403 may be a reshapable portion which can be reshaped. Preferably, the reshapable portion is in the shape of a flat plate, a prism or the like.

The outer diameter of the body portion 432 of the core wire 403 is not particularly limited, and is preferably about 0.3 to 1.0 mm, more preferably about 0.4 to 0.7 mm.

The outer diameter of the small-diameter portion 436 of the core wire 403 is not particularly limited, though is preferably about 0.05 to 0.3 mm, more preferably about 0.1 to 0.2 mm. The outer diameter of the small-diameter portion 436 may not necessarily be constant. For example, the outer diameter of the small-diameter portion 436 may gradually decrease along the distal direction.

In addition, the length of the tapered portion 434 varies depending on the use and the kind of guide wire 401, and is not particularly limited. The length of the tapered portion 434 may be preferably about 10 to 300 mm, more preferably about 30 to 250 mm.

The length of the small-diameter portion 436 is not particularly limited, though is preferably about 0 to 100 mm, more preferably about 10 to 50 mm.

The taper angle of the tapered portion 434 (i.e., the rate of reduction of the outer diameter of the tapered portion 434) may be constant along the longitudinal direction of the core wire 403, or may vary at some portion along the longitudinal direction. In addition, the tapered portion 434 is not limited to only one tapered portion; two or more tapered portions may be provided.

Examples of the material which can be used to form the core wire 403 include various metallic materials such as stainless steel, Ni—Ti alloys, Ni—Al alloys, Cu—Zn alloys and other superelastic alloys, and resin materials having comparatively high stiffness, which may be used either singly or combination of two or more of them.

In addition, the coil 404 is disposed around the outer periphery of a distal portion of the core wire 403. In the illustrated embodiment, the coil 404 is disposed around the outer periphery of the small-diameter portion 436 of the core wire 403 and the outer periphery of the portion of the core wire extending from the proximal end of the small-diameter portion 436 to a region in an intermediate part of the tapered portion 434. The coil 404 is a member obtained by winding a wire in a helical shape, and is so disposed as to cover a distal-side portion of the core wire 403. In the illustrated configuration, the distal-side portion of the core wire 403 is positioned in a substantially central part of the inside of the coil 404. The distal-side portion of the core wire 403 is located in the coil 404 so that the outer surface of the distal-side portion of the core wire 403 does not make contact with the inner surface of the coil 404.

The proximal end of the coil 404 is located at an intermediate part of the tapered portion 434 of the core wire 403, and the marker 412 is located on the proximal side relative to the intermediate part. This helps avoid positional interference between the coil 404 and the marker 412, while the guide wire 401 is simple in structure. Incidentally, the marker 412 may be formed ranging to the outer peripheral side of the coil 404. In other words, the marker 412 may be formed and positioned to longitudinally overlap the coil 40 in side view.

In the illustrated embodiment, the coil 404 is configured so that gaps exist between immediately adjacent windings of the helical wire when no external force is applied to the coil. However, the coil 404 may also be configured sop that the immediately adjacent windings of the helical wire are disposed more closely without any gap between immediately adjacent windings.

The coil 404 is preferably formed of a metallic material. Examples of the metallic material for use to form the coil 404 include stainless steel, superelastic alloys, cobalt alloys, noble metal such as gold, platinum, tungsten, etc., alloys containing these noble metals, for example, platinum-iridium alloys, and so on. Particularly, where the coil 404 is formed of a radiopaque material such as noble metals, the guide wire 401 can have radiopacity, so that the guide wire 401 can be inserted into a living body while checking the position of its distal portion under fluoroscopic observation. In addition, the coil 404 may be formed of different materials on the distal side and on the proximal side. For instance, the coil 404 may be composed of a coil of a radiopaque material on the distal side and a coil of a comparatively radiolucent material, for example stainless steel, on the proximal side. The overall length of the coil 404 is not particularly limited, though is preferably about 5 to 500 mm. While this illustrated embodiment of the coil 404 is formed by use of a wire having a circular cross-section, the configuration of the coil is not limited in this regard. Indeed, the cross-sectional shape of the wire may be other shapes, such as an ellipse, a tetragon, a rectangle, etc.

The proximal portion and the distal portion of the coil 404 are firmly attached to the core wire 403 by fixing materials 481, 482, respectively.

These fixing materials 481, 482, i.e., the two fixing portions for fixing the core wire 403 and the coil 404 to each other, are provided on the distal side relative to the annular member 405, and are not in contact with the annular member 405. This makes it possible to inhibit or prevent the conduction of electrical current between the core wire 403 and the annular member 405 from being made through the fixing material 481. Accordingly, conduction of the electrical current between the outer surface of the guide wire and the core wire 403 can be inhibited or prevented from occurring.

The fixing materials 481, 482 are each composed of solder or a brazing metal. Incidentally, the material constituting each of the fixing materials 481, 482 is not limited to solder and may be, for example, an adhesive. Further, the method of fixing the coil 404 is not limited to the use of the fixing materials; for example, welding may be adopted as the fixing method.

In addition, the guide wire 401 has the resin coating layer 406 covering a distal portion of the core wire 403, the coil 404, and the outer peripheries of the fixing materials 481, 482. The resin coating layer 406 is in intimate contact with the outer periphery of the distal portion of the core wire 403.

In the illustrated embodiment shown in FIG. 16, the resin coating layer 406 has entered into the inside of the coil 404. However, the resin coating layer 406 may not necessarily have entered into the inside of the coil 404.

The resin coating layer 406 can be formed for various purposes. An example of the purpose is to enhance safety in inserting the guide wire 401 into a blood vessel or the like. For this purpose, the resin coating layer 406 is preferably composed of a flexible material. Examples of the material include polyolefins such as polyethylene, polypropylene, etc., polyvinyl chloride, polyesters (PET, PBT, etc.), polyamides, polyimides, polyurethane, polystyrene, silicone resins, thermoplastic elastomers such as polyurethane elastomer, polyester elastomer, polyamide elastomer, etc., various rubber materials such as latex rubber, silicone rubber, etc., and composite materials obtained by combining two or more of these materials.

Where the resin coating layer 406 is composed of one of the above-mentioned thermoplastic elastomers and various rubbers, the flexibility of the distal portion of the guide wire 401 is more enhanced. In this case, therefore, it is possible to more securely inhibit or prevent the distal portion from injuring the inner wall of a blood vessel or the like at the time of insertion into the blood vessel or the like, and helps contribute to providing quite high safety.

Particles composed of a radiopaque material may be dispersed in the resin coating layer 406. This helps impart radiopacity to the guide wire 401 so that the guide wire 401 can be inserted into a living body while checking the position of its distal portion under fluoroscopic observation. The material constituting the particles is not particularly limited, provided it is a radiopaque material. For example, noble metals such as gold, platinum, tungsten, etc. and alloys containing them, for example platinum-iridium alloys, can be used as the material of the particles.

The thickness of the resin coating layer 406 is not particularly limited, and may be appropriately set based on, for example, the purpose of forming the resin coating layer 406, the material constituting the layer, the method of forming the layer, etc. Usually, the thickness is preferably about 30 to 300 μm, more preferably about 50 to 200 μm. When the thickness of the resin coating layer 406 is too small, the purpose of forming the resin coating layer 406 may be attained insufficiently. On the other hand, when the thickness of the resin coating layer 406 is too large, it may influence the physical properties of the wire body 402. The resin coating layer 406 may be a laminate of two or more layers.

In addition, the distal surface of the resin coating layer 406 is rounded. This makes it possible to more securely prevent the distal surface of the resin coating layer 406 from injuring the inner surface of a blood vessel or the like at the time of inserting the guide wire 401 into the blood vessel or the like.

The guide wire 401 includes, on the proximal side of the resin coating layer 406, the annular member 405. This annular member 405 fills up the stepped space between the proximal portion of the resin coating layer 406 and the wire body 402. The outer diameter of the proximal end of the resin coating layer 406 is greater than the outer diameter of the wire body 402 at the proximal end of the resin coating layer 406, and the stepped space is generated due to the difference in outer diameter.

The outer diameter of the distal end 452 of the annular member 405 is substantially equal to the outer diameter of the proximal end of the resin coating layer 406. The distal end face 453 of the annular member 405 is joined (adhered) to the proximal end face 461 of the resin coating layer 406. In this case, the resin coating layer 406 is inhibited or prevented from extending toward the proximal side beyond the distal end 452 of the annular member 405 to coat the annular member 405. In other words, a continuous surface without any step is formed between the distal end 452 of the annular member 495 and the proximal end of the resin coating layer 406.

In addition, the outer diameter of the annular member 405 is gradually decreased from the distal side toward the proximal side (along the proximal direction), and the outer diameter of the annular member 405 is smaller at the proximal end 451 than at the distal end 452. The outer diameter of the proximal end 451 of the annular member 405 is substantially equal to the outer diameter of the coating layer 407 on the wire body 402 at the proximal end 451 of the annular member 405. In other words, a continuous surface free of any step is formed between coating layer 407 on the wire body 402 and the proximal end 451 of the annular member 405. The outer diameter of the proximal end 451 of the annular member 405 is smaller than the outer diameter of the body portion 432 of the core wire 403. The annular member 405 has a length of 0.5 to 15 mm.

The inner diameter of the annular member 405 is larger at the proximal end 451 than at the distal end 452. This is because the annular member 405 is located on the tapered portion 434 of the core wire 403, as will be described later. The inner diameter at the proximal end 451 may be equal to the inner diameter at the distal end 452.

By virtue of the presence of the annular member 405, the proximal portion of the resin coating layer 406 can be inhibited or prevented from being caught by a medical implement used in combination with the guide wire 401, for example, by the distal end of a catheter or by the riser base of an endoscope. Therefore, the resin coating layer 406 can be inhibited or prevented from being peeled off. In addition, the slidability of the guide wire 401 can be prevented from being lowered due to the above-mentioned step.

The angle of inclination θ of the annular member 405, in this embodiment is constant along the longitudinal direction of the core wire 403. The inclination angle θ may vary along the longitudinal direction at some portions. The angle of inclination θ is preferably not more than 30°, more preferably about 2 to 25°, and further preferably about 5 to 20°. This helps ensure that the annular member 405 can be prevented from being caught by a medical implement used in combination with the guide wire 401, for example by the distal end of a catheter or by the riser base of an endoscope.

The hardness of the annular member 405 is preferably greater than the hardness of the resin coating layer 406. This also helps ensure that the annular member 405 can be prevented from being caught by a medical implement used in combination with the guide wire 401, for example by the distal end of a catheter or by the riser base of an endoscope.

One or both of the distal end faces 453 and the inner peripheral surface of the annular member 405 may be roughened. When the distal end face 453 of the annular member 405 is roughened, its adhesion to the resin coating layer 406 is enhanced. When the inner peripheral surface is roughened, its adhesion to the fixing member 409 (described later) is enhanced.

In addition, the material constituting the annular member 405 is not limited to a specific material. Examples of suitable materials include various resin materials and various metallic materials and the like. For instance, the same material as that of the resin coating layer 406 may be used, or a material different from the material of the resin coating layer 406 may be used.

The annular member 405 is preferably formed by use of a metallic material or a resin material, particularly a metallic material. Examples of the metallic material which can be used to form the annular member 405 include stainless steel, titanium, titanium alloys, Ni—Ti alloys, aluminum, gold, and platinum. When a noble metal such as gold and platinum or an alloy thereof is used, radiopacity is enhanced. In addition, when the annular member 405 is made of a metallic material, the outer periphery of the annular member 405 may be covered with a coating layer (not shown). The material constituting the coating layer is not limited to a particular material. Examples of materials that can be sued include various resin materials, various ceramics, various metallic materials and the like. An insulating material is preferable. When the annular member 405 is formed by use of a hard resin material, examples of the hard resin material include polycarbonate, polyamide, polyethylene terephthalate, polyacetal, and polyphenylene sulfide.

In addition, the annular member 405 is firmly attached to the core wire 403 by the fixing material 409 on the outer periphery of the core wire 403.

The fixing material 409 is preferably composed of an adhesive, particularly an insulating adhesive. This makes it possible to insulate the core wire 403 and the annular member 405 from each other. Consequently, for example in the case where a medical implement used by passing an electric current is disposed along the guide wire 401, troubles such as leakage of current from the outer surface of the annular member 405 can be inhibited from or prevented from occurring.

The fixing material 409 is not limited to an adhesive. For example, in the case where the annular member 405 is a metallic material, a solder (brazing metal) or the like may be used as the fixing material 409. In addition, the method of fixing the annular member 405 is naturally not limited to the use of the fixing material.

The annular member 405 is located at the tapered portion 434 of the core wire 403 (wire body 402). While the annular member 405 is entirely located at the tapered portion 434 in the illustrated embodiment, this is not limitative. A configuration may also be adopted in which only a part of the annular member 405 is located at the tapered portion 434.

The annular member 405 moderates the difference in flexural rigidity of the wire body 402 between the proximal side and the distal side of the annular member 405. Specifically, as discussed above, the outer diameter of the core wire 403 at the tapered portion 434 decreases gradually along the distal direction, and the rigidity of the core wire 403 is gradually lowered along the distal direction. On the other hand, the resin coating layer 406 is provided on the wire body 402 on the distal side of the annular member 405. In the absence of the annular member 405, the rigidity by just the thickness of the resin coating layer 406 increases abruptly at the proximal end of the resin coating layer 406, so that kinking is liable to occur. In this guide wire 401, however, the annular member 405 helps ensure that the abrupt increase in rigidity at the proximal end of the resin coating layer 406 is less likely to occur and is preferably prevented, whereby kinking at the proximal end of the resin coating layer 406 can be inhibited or prevented from occurring.

The guide wire 401 disclosed here is applicable not only to guide wires used under fluoroscopy, but also to guide wires used together with an endoscope. More specifically, the guide wire 401 here has useful application as a guide wire by which a catheter inserted in the lumen of an endoscope is guided to a target site of an intracorporeal lumen or the like (hereinafter, such a guide wire is referred to as "trans-endoscopic guide wire"). In this embodiment, the case where the guide wire 401 is applied to a trans-endoscopic guide wire will be described as a representative use.

In the trans-endoscopic guide wire, the outer surface of the guide wire 401 is provided with a visual marker indicating the intracorporeal position of the guide wire 401, and the visual marker is visually recognized through an endoscope. In this embodiment, the marker 412 is the visual marker. The marker 412 is provided on the outer periphery of the wire body 402, with a primary layer 413 between the marker 412 and the outer surface of the wire 403 as shown in FIG. 16. The guide wire 401 is also provided with the coating layer 407 covering the marker 412 and the primary layer as illustrated in FIG. 16.

As shown in FIG. 16, the marker 412 includes a first line-forming portion 421 and a second line-forming portion 422. The first line-forming portion 421 is in the form of a helically wound member. In the illustrated embodiment, the first line-forming portion 421 is provided over the whole circumference of the wire body 402 (i.e., the first line-forming portion 421 extends completely around the circumference of the wire body 402, and preferably extends completely around the circumference of the wire body 402 several times). In addition, the first line-forming portion 421 is a loose winding in which gaps are left between the immediately adjacent lines.

The second line-forming portion 422 is also in a helical shape or configuration, like the first line-forming portion 421. However, the helical winding direction of the second line-forming portion 422 is opposite to the winding direction of the helix of the first line-forming portion 421. As a result, the second line-forming portion 422 is provided over the whole circumference of the wire body 402 (i.e., the second line-forming portion 422 extends completely around the circumference of the wire body 402, and preferably extends completely around the circumference of the wire body 402 several times). Like the first line-forming portion 421, the second line-forming portion 422 is a loose winding in which gaps are left between the immediately adjacent lines.

With the first line-forming portion 421 and the second line-forming portion 422 provided in this manner, the line-forming portions intersect each other at a plurality of locations so that the marker 412 as a whole is grid-like in shape or configuration (layout).

Figure 17:
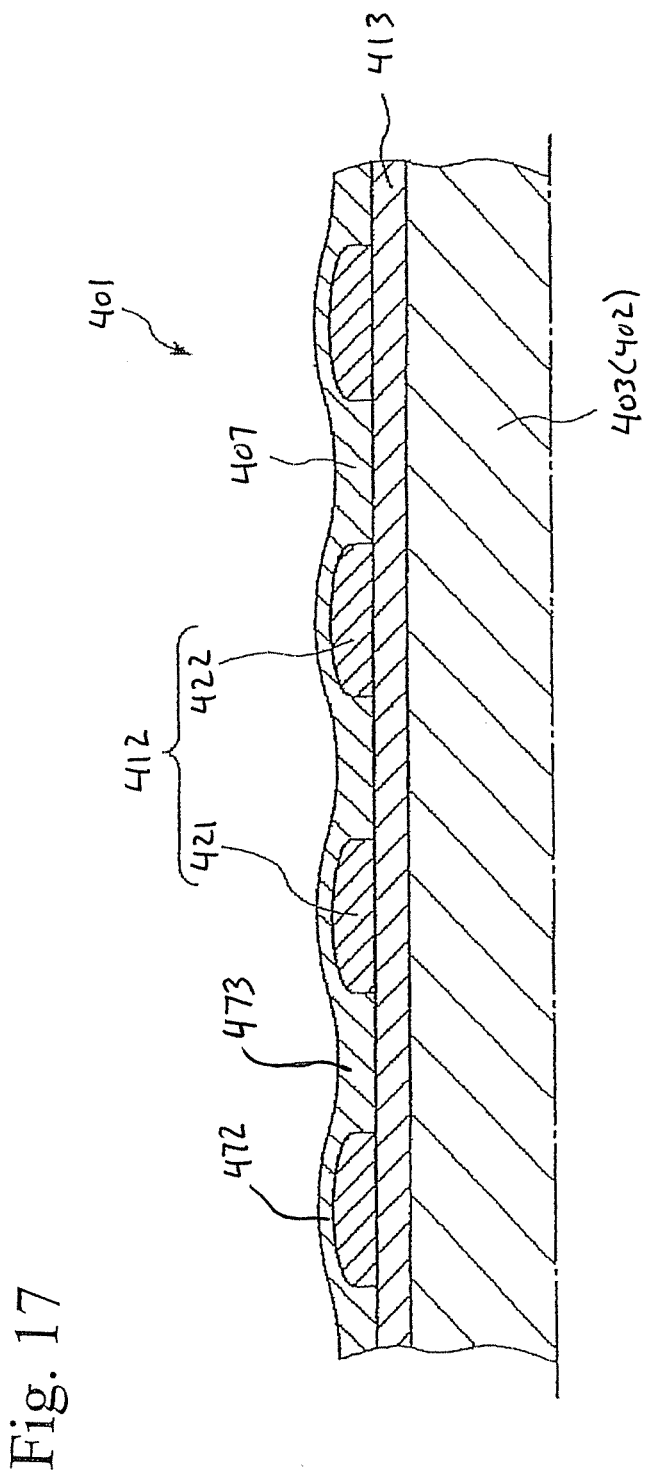
FIG. 17 is a longitudinal cross-sectional view of region [A] surrounded by the dot-dash line in FIG. 16.

As shown in FIG. 17, the first line-forming portion 421 and the second line-forming portion 422 are roughly semi-elliptic in vertical sectional shape, with the top portion curved to form a projected shape. The height of the first line-forming portion 421 and the second line-forming portion 422 is not limited to a specific value. By way of example, the height is preferably 3 to 8 μm, more preferably 3 to 5 μm.

When the guide wire 401 is extracorporeally observed through an endoscope, the marker 412 appears as shown in FIGS. 20A, 20B, 21A, 21B. A case where the guide wire 401 is rotated about its axis is described referring to FIGS. 20A and 20B. A situation in which the guide wire 401 is moved in its axial direction will be described referring to FIGS. 21A and 21B.

Figure 20A:
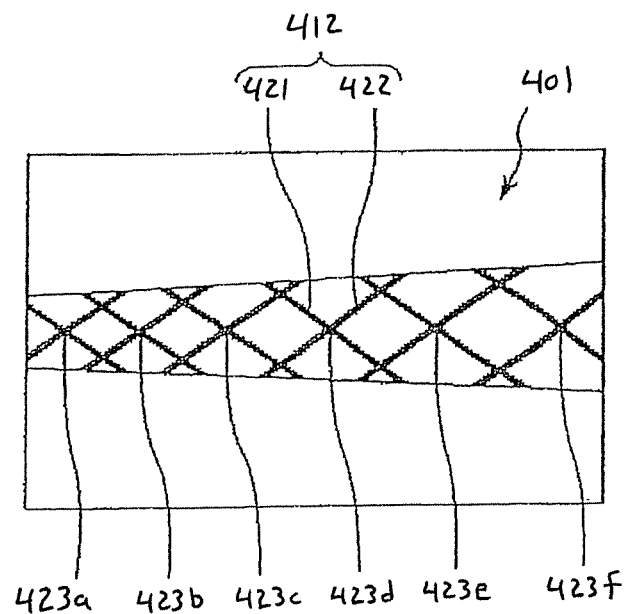
FIGS. 20A and 20B illustrate the process of changing the marker when the guide wire is rotated about its axis.
Figure 20B:
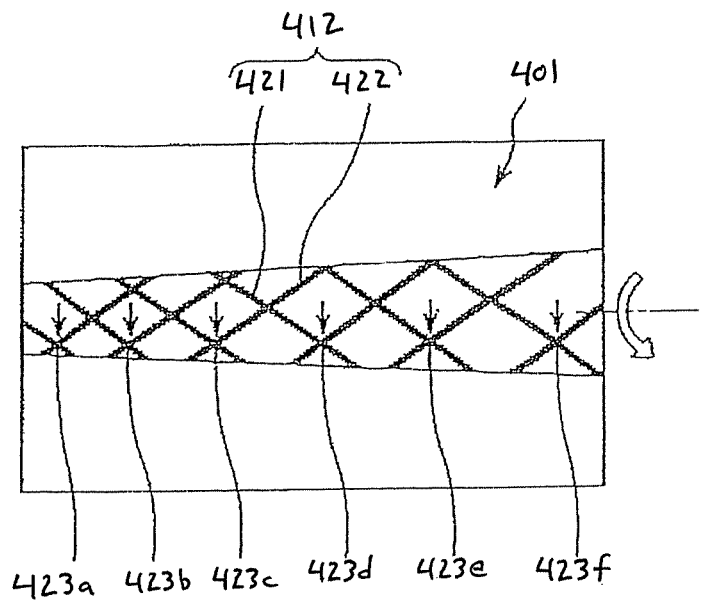

First, the case where the guide wire 401 is rotated about its axis will be described. FIG. 20A shows the condition before rotation of the guide wire 401. When the guide wire 401 then rotated by a predetermined amount in the direction of arrow in the figure, the condition shown in FIG. 20B results.

As mentioned above, the marker 412 has a plurality of intersecting parts 423 where the first line-forming portion 421 and the second line-forming portion 422 intersect each other. Here, considering the intersecting parts 423a, 423b, 423c, 423d, 423e and 423f of the first line-forming portion 421 and the second line-forming portion 422 which can be observed (as in FIG. 20A) in practice, the intersecting parts 423a-423f in FIG. 20B have been moved downwards in the figure, as compared with those same intersecting parts in the condition shown in FIG. 20A.

The visual checking of the marker 412 in this manner helps ensure that when the guide wire 401 is rotated about its axis by applying torque to the guide wire 401, the fact that "the guide wire 401 has been rotated" can be reliably confirmed.

In addition, when the guide wire 401 is rotated in the opposite direction, the intersecting parts 423a-423f are moved upwards in the figure from the condition shown in FIG. 20A. This makes it possible to confirm whether the guide wire 401 is being rotated upwards or downwards in the figure, i.e., to confirm the rotating direction of the guide wire 401.

Figure 21A:
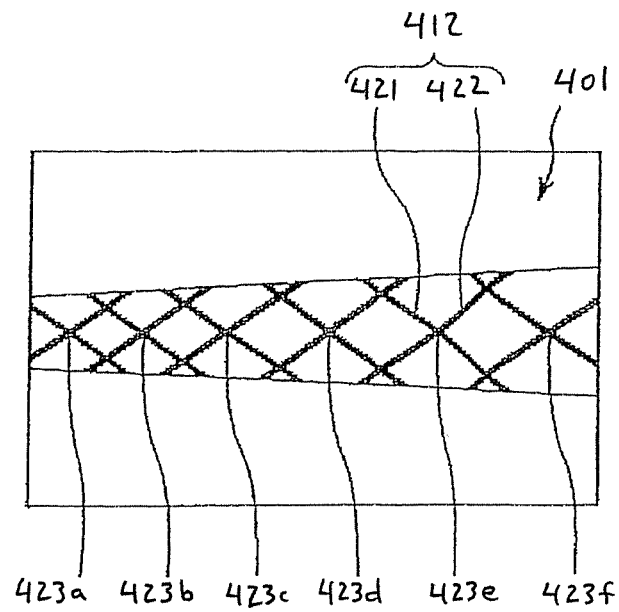
FIGS. 21A and 21B illustrate the process of changing the marker when the guide wire is moved along its axial direction.

Now, the case where the guide wire 401 is moved in the axial direction is discussed. FIG. 21A shows the condition before movement of the guide wire 401. When the guide wire 401 is moved by a predetermined distance in the direction of the arrow noted in the figure, the condition shown in FIG. 21B results.

Figure 21B:
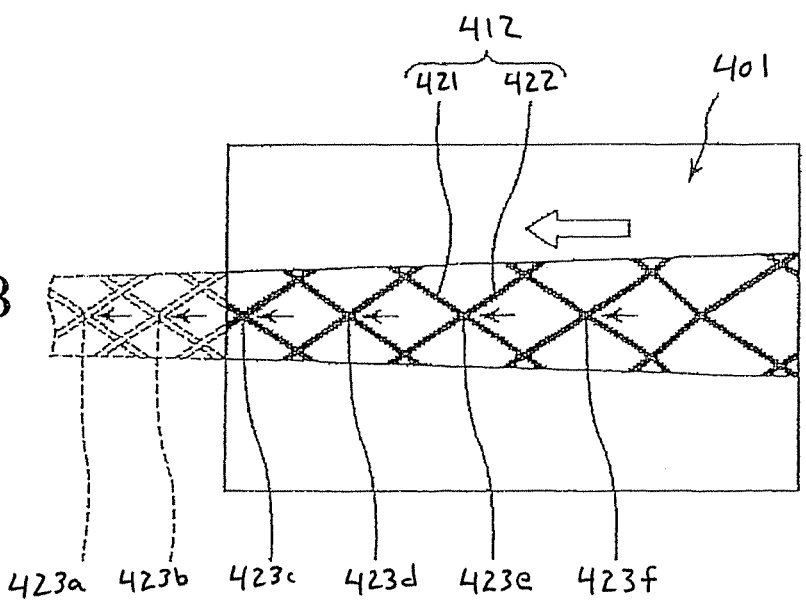

Here, considering the intersecting parts 423*a*-423*f* of the first line-forming portion 421 and the second line-forming portion 422 which can be observed as in FIG. 21A in practice, the intersecting parts 423*a*-423*f* in FIG. 21B have moved in the distal direction (leftwards in the figure) from the condition shown in FIG. 21A. In addition, the intersecting parts 423*a* and 423*b* come out of the field of view.

Since the marker 412 can thus be visually checked, it is possible with a configuration disclosed by way of example here to reliably confirm that when the guide wire 401 is pushed in the distal direction and is thereby moved along the axial direction, "the guide wire 401 has been moved."

In addition, when the guide wire 401 is moved in the direction opposite to the above by pulling it, the intersecting parts 423*a*-423*f* are moved in the proximal direction (rightward in the figure) from the condition shown in FIG. 21A. As a result, it is possible to confirm whether the guide wire 401 is being moved in the distal direction or the proximal direction, i.e., to confirm the moving direction of the guide wire 401.

As has been described above, when the guide wire 401 is moved along its axis or rotated about its axis, the above-mentioned change of the marker 412 makes it possible to securely distinguish whether the practical displacement of the guide wire 401 is a movement or rotation.

In the case of a guide wire having a single helical marker as in a known guide wire, even if the guide wire is rotated about its axis by applying torque, the operator would have an illusion that the guide wire is being advanced or retracted, against the operator's will to cause rotation. In using the guide wire 401 here, on the other hand, such an illusion can be reliably inhibited or prevented from occurring, and excellent steerability is exhibited.

As shown in FIG. 16, at the same position in the axial direction of the wire body 402, specifically the body portion 432 and the tapered portion 434 of the wire body 402, the pitch of the helix of the first line-forming portion 421 and the pitch of the helix of the second line-forming portion 422 are equal. This results in the plurality of intersecting parts 423 being favorably dispersed in the region in which the marker 412 is formed, and, therefore visibility of the intersecting parts 423 is enhanced. In addition, there is a merit in that the rotation of the guide wire 401 and the pushing/pulling operation of the guide wire 401 can be relatively easily discriminated or differentiated from each other.

In addition, the marker 412 is provided with a decreasing-pitch portion 424 where the pitch of the helix of the first line-forming portion 421 and the second line-forming portion 422 in the tapered portion 434 is gradually decreased along the distal direction. By checking the decreasing-pitch portion 424, it is possible to grasp that the wire body 402 is smaller in diameter and higher in flexibility at that portion.

As shown in FIG. 16 (and in FIGS. 20A, 20B, 21A and 21B also), the width of the first line-forming portion 421 and the width of the second line-forming portion 422 are equal. This helps ensure that, in forming the marker 412, an operation of forming the line-forming portions while setting different widths can be omitted. Therefore, the marker 412 can be formed more easily.

Incidentally, the width of the first line-forming portion 421 and the second line-forming portion 422 is preferably 0.5 to 2 times, more preferably 0.5 to 1.5 times, the diameter of the wire body 402. When the width exceeds the upper limit of the numerical value range just-mentioned, halation may occur, depending on the intensity of light radiated from the endoscope at the time of visually checking the marker 412.

The first line-forming portion 421 and the second line-forming portion 422 may be the same or different in color. Preferably, however, the line-forming portions 421, 422 are different in color. In the case where the first line-forming portion 421 and the second line-forming portion 422 are different from each other in color, when the guide wire 401 is rotated about its axis, the rotating direction can be grasped as follows. If the first line-forming portion 421 and the second line-forming portion 422 are visually recognized as moving away from each other, the rotation in question is found to be rotation in the direction of the arrow in FIGS. 20A and 20B. On the other hand, if the first line-forming portion 421 and the second line-forming portion 422 are visually recognized as moving closer to each other, the rotation is found to be rotation in the opposite direction, namely in the direction opposite to the direction of the arrow in FIGS. 20A and 20B.

Figure 18:
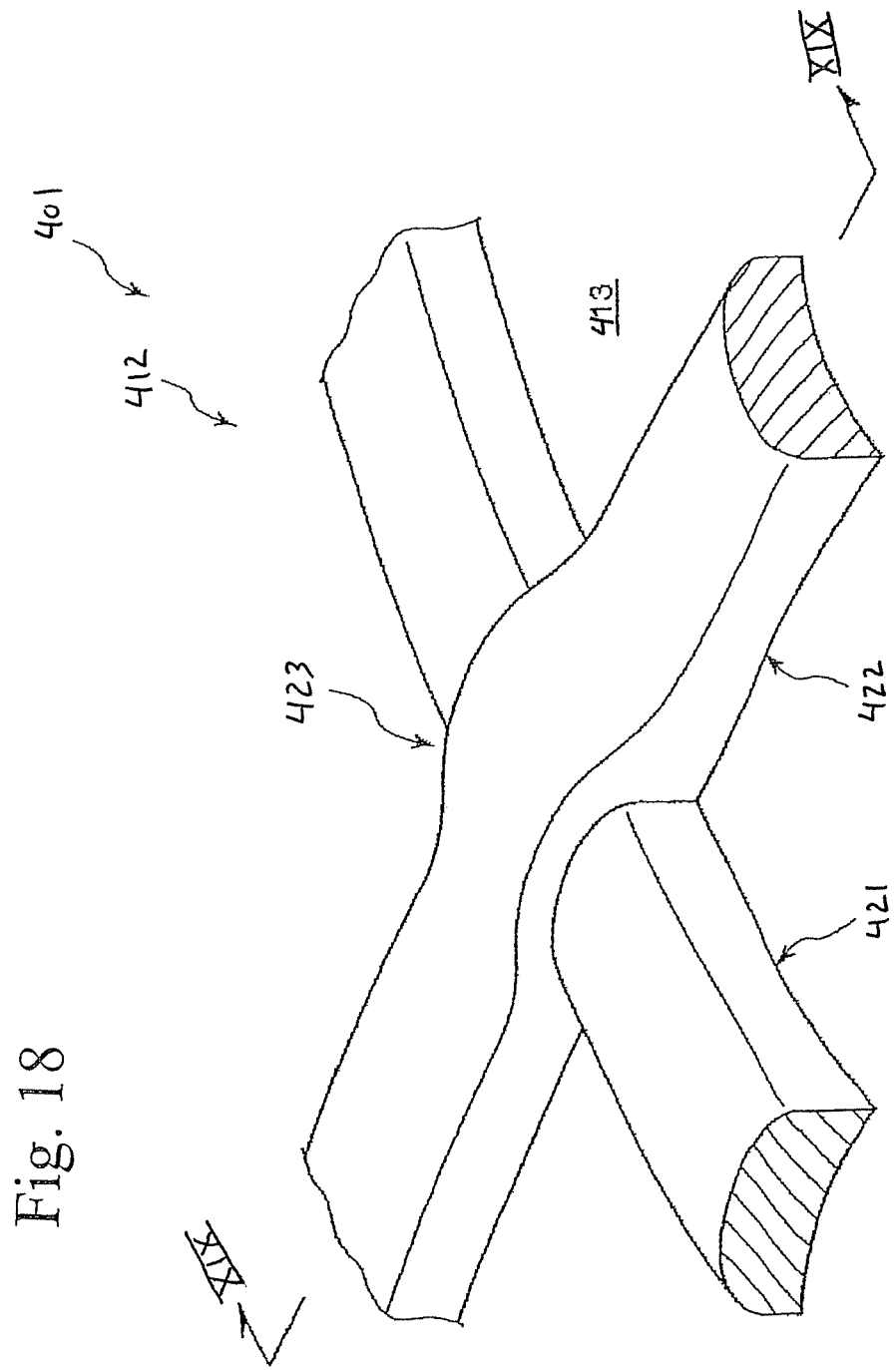
FIG. 18 is a perspective view of a marker in the guide wire shown in FIG. 16.

As shown in FIG. 18, in the marker 412, the height of the intersecting parts 423 is greater than the height of the other portions, i.e., greater than the height of the portions exclusive of the intersecting parts 423 of the first line-forming portion 421 and the second line-forming portion 422. The height of the intersecting parts 423 is not particularly limited, though is preferably, by way of example, 3 to 10 µm, more preferably 5 to 8 µm.

Figure 19:
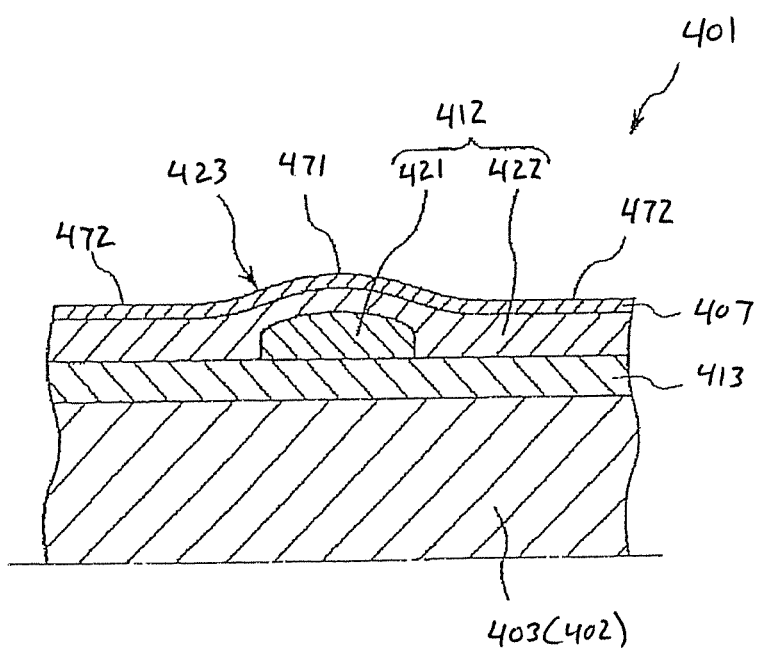
FIG. 19 is a cross-sectional view of the guide wire taken along the section line XIX-XIX in FIG. 3.

As mentioned above, the marker 412 is covered with the coating layer 407 as illustrated in FIG. 19. The coating layer 407 forming an outer surface of the guide wire 401 is raised in the areas where the intersecting parts 423 of the marker 412 are arranged than in the areas where the marker 412 is not arranged. Specifically, raised portions 471 are formed in the areas where the intersecting parts 423 are arranged, whereas recesses 472 are formed in the areas where only the second line-forming portion 422 is arranged as shown in FIG. 19 and recesses 473 are formed in the areas where neither the first line-forming portion 421 nor the second line-forming portion 422 is arranged as shown in FIG. 17. The areas where neither the first line-forming portion 421 nor the second line-forming portion 422 is arranged are more recessed than the areas where only the second line-forming portion 422 is arranged. This is because the thickness of the coating layer 407 is comparatively small, so that the outer surface of the resin layer 407 is influenced by the presence of the intersecting parts 423, to be raised corresponding to the shape and pattern of the intersecting parts 423. The longitudinally extending region of the guide wire at which the intersecting parts 423 are arranged constitutes a bulge-forming region, and the marker 112 is a bulge-forming layer.

The area of contact between the outer surface of the coating layer 407 and the lumen of a catheter or the lumen of an endoscope is reduced, and the frictional resistance is thereby reduced, leading to enhanced slidability and better steerability of the guide wire 401.

In addition, the raised portions 471 and the hollowed or recessed portions 472 (undulating surface) are not formed by direct working of the coating layer 407, but are formed under the influence of the intersecting parts 423 underlying the coating layer 407. Therefore, the outer surface of the coating layer 407 is a smooth surface which is free of sharp corner portions or crest portions. Specifically, according to the roundness of the top portions of the first line-forming portion 421 and the second line-forming portion 422, the raised portions 471 are rounded similarly. This further enhances slidability, and helps enhance a relatively high degree of safety.

The first line-forming portion 421 and the second line-forming portion 422 are each formed of a material containing a resin and a pigment. The material constituting the first line-forming portion 421 and the material constituting the second line-forming portion 422 are substantially the same. Therefore, the material constituting the first line-forming portion 421 will be described below representatively.

The color of the first line-forming portion 421 is determined mainly by the kind and properties of the pigment contained in the first line-forming portion 421, the composition and properties, particularly tone, of the resin material, and the content of the pigment. Therefore, by regulating these factors, it is possible to relatively freely set the color of the first line-forming portion 421.

Here, to recognize the motion of the guide wire 401 through an endoscope, the color of the first line-forming portion 421 is an important factor, and its combination with the color of the primary layer 413 serving as a substrate should be taken into account.

As an example, the primary layer 413 is silver, grey or black in color and the first line-forming portion 421 is red or yellow. In this example, the difference in color brightness between these two sets of colors is large, leading favorably to a high visibility of the first line-forming portion 421. It is preferable that both colors have a relation to complement each other, leading favorably to a high visibility of the first line-forming portion 421. It is particularly preferable to select a combination of colors which gives a clear contrast, such as a combination of black or another deep color (for example charcoal grey, dark brown, dark blue, or purple) with yellow, yellowish green, orange or the like, and a combination of blue with red, orange, pink or the like. In addition, a combination of akin colors with different shades may also be used, for example a combination of dark blue with light blue or a combination of reddish brown with pink.

The resin contained in the material constituting the first line-forming portion 421 is not particularly limited, though is preferably the following (1) or (2).

(1) The resin contained in the material constituting the first line-forming portion 421 may preferably be a heat-resistant resin having a melting point of not less than 200° C., more preferably a resin having a melting point of about 200 to 300° C.

Examples of the resin having a melting point of not less than 200° C. include polysulfone, polyimide, polyetherether ketone, polyarylene ketone, polyphenylene sulfide, polyarylene sulfide, polyamide-imide, polyether-imide, polyimide-sulfone, polyarylsulfone, polyarylether-sulfone, polyester, polyether-sulfone, and fluororesins such as polytetrafluoroethylene (PTFE), ethylene-tetrafluoroethylene copolymer (ETFE), etc., which may be used either singly or in combination of two or more of them.

(2) The resin contained in the material constituting the first line-forming portion 421 may preferably be a thermosetting resin.

Examples of the thermosetting resin include epoxy resins, phenolic resins, polyesters (unsaturated polyesters), polyimides, silicone resins, polyurethane, etc., which may be used either singly or in combination of two or more of them.

The content of the pigment in the first line-forming portion 421 varies depending on the kind and properties of the pigment, and the composition and properties of the resin material. To obtain a good color, the content of the pigment is preferably about 10 to 99 wt. %, more preferably about 20 to 50 wt. %, based on the whole weight of the first line-forming portion 421.

The pigment in the first line-forming portion 421 preferably is dispersed uniformly. However, the pigment may be locally present, for example on the outer surface side in the first line-forming portion 421. The pigment may be either an inorganic pigment or an organic pigment, the inorganic pigment being preferred from the viewpoint of heat resistance. Examples of the inorganic pigment which can be used include carbon black, mica, titanium dioxide, nickel-titanium yellow, Prussian blue, Milori blue, cobalt blue, ultramarine, viridian, etc. Incidentally, these pigments may be used either singly or in mixture of two or more of them. The particle diameter of the pigment is not particularly limited, though is preferably, for example, 0.3 to 5 μm, more preferably 0.5 to 3 μm.

Set forth below is a description of an example of a way to form a marker 412 as described above. As between the first line-forming portion 421 and the second line-forming portion 422, the first line-forming portion 421 is formed prior to the second line-forming portion 422.

To form the first line-forming portion 421, masking tape is first helically wound around and adhered to the portion of the core wire 403 other than the region where the first line-forming portion 421 is to be formed. The wire core is thus masked in the area other than where the first line-forming portion 421 is to be formed. The portion of the first line-forming portion 421 which is not masked is a helically extending unmasked portion.

Next, the resin material in a liquid state containing the pigment added thereto (this material will hereinafter be referred to as "liquid material") is supplied to coat the exposed portion of the core wire 403 at which the masking tape is not present. Examples of the method of coating include a spraying method and a dipping method.

Subsequently, the liquid material thus applied is dried. Thereafter, the masking tape is removed.

By the steps as above, the first line-forming portion 421 can be formed. Next, the second line-forming portion 422 is formed. To form the second line-forming portion 422, a masking tape is first helically wound around the core wire 403 which has been provided thereon with the first line-forming portion 421. The masking tape is wound in an opposite direction and adhered to the portion of the core wire 403 other than the region where the second line-forming portion 422 is to be formed. The wire core is thus masked in the area other than where the second line-forming portion 422 is to be formed. The portion of the second line-forming portion 422 which is not masked is a helically extending unmasked portion.

Next, in the same manner as in forming the first line-forming portion 121, a liquid material is supplied to coat the exposed portion of the core wire 3 where the masking tape is not wound.

Subsequently, the liquid material thus applied is dried. Thereafter, the masking tape is removed.

By the method described above, the second line-forming portion 422 partly superposed on the first line-forming portion 421 is formed. Therefore, a grid-like marker 412 with the intersecting raised parts 423 id formed relatively easily and assuredly.

The first line-forming portion 421 and the second line-forming portion 422 may each be formed either singly or in plural. In addition, the number of the first line-forming portion(s) 421 and the number of the second line-forming portion(s) 422 may be the same or different.

While the first line-forming portion 421 and the second line-forming portion 422 are the same in width in the embodiment shown in FIG. 16, the first and second line-forming portion 421, 422 are not limited in this regard. For example, the first line-forming portion 421 and the second line-forming portion 422 may possess different widths.

As shown in FIGS. 17 and 19, the coating layer 407 covers the marker 412 and the primary layer 413. The coating layer 407 has such a degree of transparency that the marker 412 can be visually recognized through the coating layer 407.

The coating layer 407 can be formed for any of various purposes. One example is to reduce the friction (sliding resistance) on the guide wire 401 and to enhance slidability of the guide wire 401, thereby enhancing steerability of the guide wire 401.

To achieve a reduction in the friction on the guide wire 401, the coating layer 407 is preferably formed by use of a material capable of reducing friction as described below. This results in the frictional resistance on the inner wall of a catheter used together with the guide wire 401 being reduced, whereby slidability of the guide wire 401 is enhanced, and steerability of the guide wire 401 in the catheter or in an endoscope is more enhanced. In addition, the lowered sliding resistance of the guide wire 401 helps ensure that when the guide wire 401 is moved and/or rotated in an endoscope or in a catheter, the guide wire 401 can be relatively reliably prevented from kinking or twisting.

Besides, the coating layer 407 is preferably composed of an insulating material. The reason is that because a distal portion of the coating layer 407 is positioned in the annular member 405 and the annular member 405 is located on the outer periphery of the coating layer 4077, it is possible by forming the coating layer 407 from an insulating material to insulate the core wire 403 and the annular member 405 from each other. Consequently, when a medical implement to be used by passing an electric current is disposed along the guide wire 401, for example, troubles such as leakage of current from the outer surface of the annular member 405 are less likely to occur, and are preferably prevented from occurring.

Examples of the insulating material capable of reducing friction include polyolefins such as polyethylene, polypropylene, etc., polyvinyl chloride, polyesters (PET, PBT, etc.), polyamides, polyimides, polyurethane, polystyrene, polycarbonate, silicone resins, fluororesins (PTFE, ETFE, PFA, etc.), and composite materials thereof.

Of the these insulating materials, particularly, the fluororesins and composite materials containing the same can be used to reduce more effectively the frictional resistance, and enhance the slidability, between the guide wire 401 and the inner wall of a catheter, thereby promising better steerability of the guide wire 401 in the catheter. In addition, this helps ensure that when the guide wire 401 is moved and/or rotated inside an endoscope, the guide wire 401 can be securely prevented from kinking or twisting.

The thickness of the coating layer 407 is not particularly limited. Preferably, for example, the thickness of the coating layer 407 is 10 to 40 μm, more preferably 20 to 30 μm.

As shown in FIGS. 16 and 18, a primary layer 413 different in color from the marker 412 is formed between the marker 412 and the wire body 402. The material constituting the primary layer 413 is not particularly limited, and may for example be the same material as that of the coating layer 407. For instance, where a fluororesin or a composite material containing the same is used as the material for forming the primary layer 413, coating of the core wire 403 with the resin material can be conducted while heating the resin material, by a method such as baking and spraying. This promises excellent adhesion between the core wire 403 and the primary layer 413. Then, the marker 412 and the coating layer 407 are firmly attached to the core wire 403 through the primary layer 413.

The thickness of the primary layer 413 is not particularly limited, though is preferably, for example, 3 to 20 μm, more preferably 5 to 10 μm.

Incidentally, the outer surface of at least a distal portion of the guide wire 401 is preferably coated with a hydrophilic material. This helps ensure that the hydrophilic material produces lubricity through wetting, whereby the friction on the guide wire 401 is reduced, and the slidability is further enhanced. Consequently, the steerability of the guide wire 401 is further enhanced.

Examples of the hydrophilic material include cellulose polymer materials, polyethylene oxide polymer materials, maleic anhydride materials (for example, maleic anhydride copolymer such as methyl vinyl ether-maleic anhydride copolymer), acrylamide polymer materials (for example, polyacrylamide, polyglycidyl methacrylate-dimethylacrylamide (PGMA-DMAA) block copolymer), water-soluble nylon, polyvinyl alcohol, polyvinyl pyrrolidone, etc.

Such a hydrophilic material, in many cases, exhibits lubricity through wetting (absorbing water), to reduce the frictional resistance (sliding resistance) between the guide wire 401 and the inner wall of a catheter (tubular body) or an endoscope which is used together with the guide wire 401. As a result, slidability of the guide wire 401 is further enhanced, leading to better slidability of the guide wire 401 in the catheter.

Figure 22:
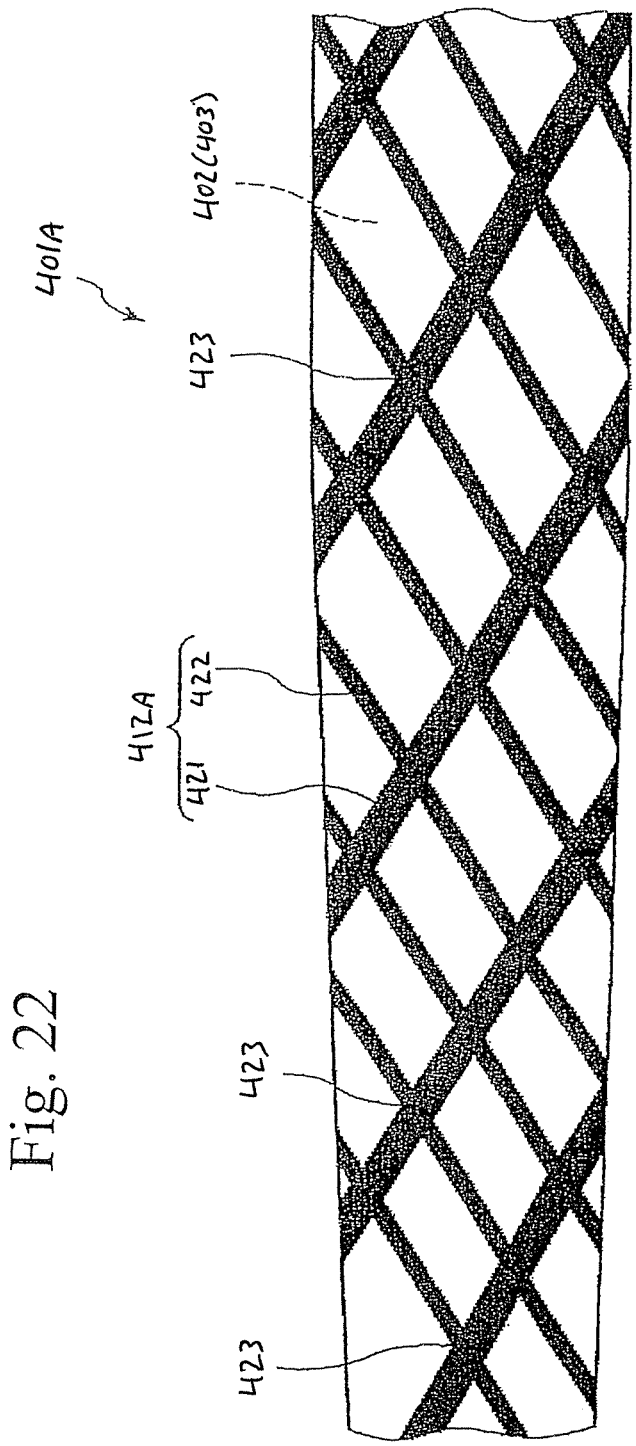
FIG. 22 is a side view showing a thirteenth embodiment of the guide wire disclosed here.

FIG. 22 is a side view of a further embodiment of the guide wire disclosed here. The following description of the guide wire embodiment shown in FIG. 22 will focus primarily upon differences between this embodiment and the embodiment described immediately above. Features in this FIG. 22 embodiment that are the same as those in the earlier embodiment are identified by common reference numerals, and a detailed discussion of such features is not repeated here.

This embodiment is the same as the embodiment shown in FIGS. 16-21, except the conditions in which the first line-forming portion and the second line-forming portion are formed.

In the marker 412A of the guide wire 401A shown in FIG. 22, the pitch of the helix of a first line-forming portion 421 and the pitch of helix of a second line-forming portion 422 are different from each other. In the configuration shown in the figure, the pitch of helix of the second line-forming portion 422 is set to be smaller than the pitch of helix of the first line-forming portion 421.

Such a configuration is effective in the case where the number of intersecting parts 423 is to be set comparatively large.

In addition, the width of the first line-forming portion 421 and the width of the second line-forming portion 422 are different from each other. In the configuration shown, the width of the first line-forming portion 421 is larger than the width of the second line-forming portion 422.

With such a configuration, the size of the intersecting parts 423 in this embodiment can be set to be greater than the size of the intersecting portions in the FIGS. 16-21 embodiment. Consequently, the visibility of the intersecting parts 423 is enhanced, that is the intersecting parts 423 can be made easier to look at or view.

Figure 23:
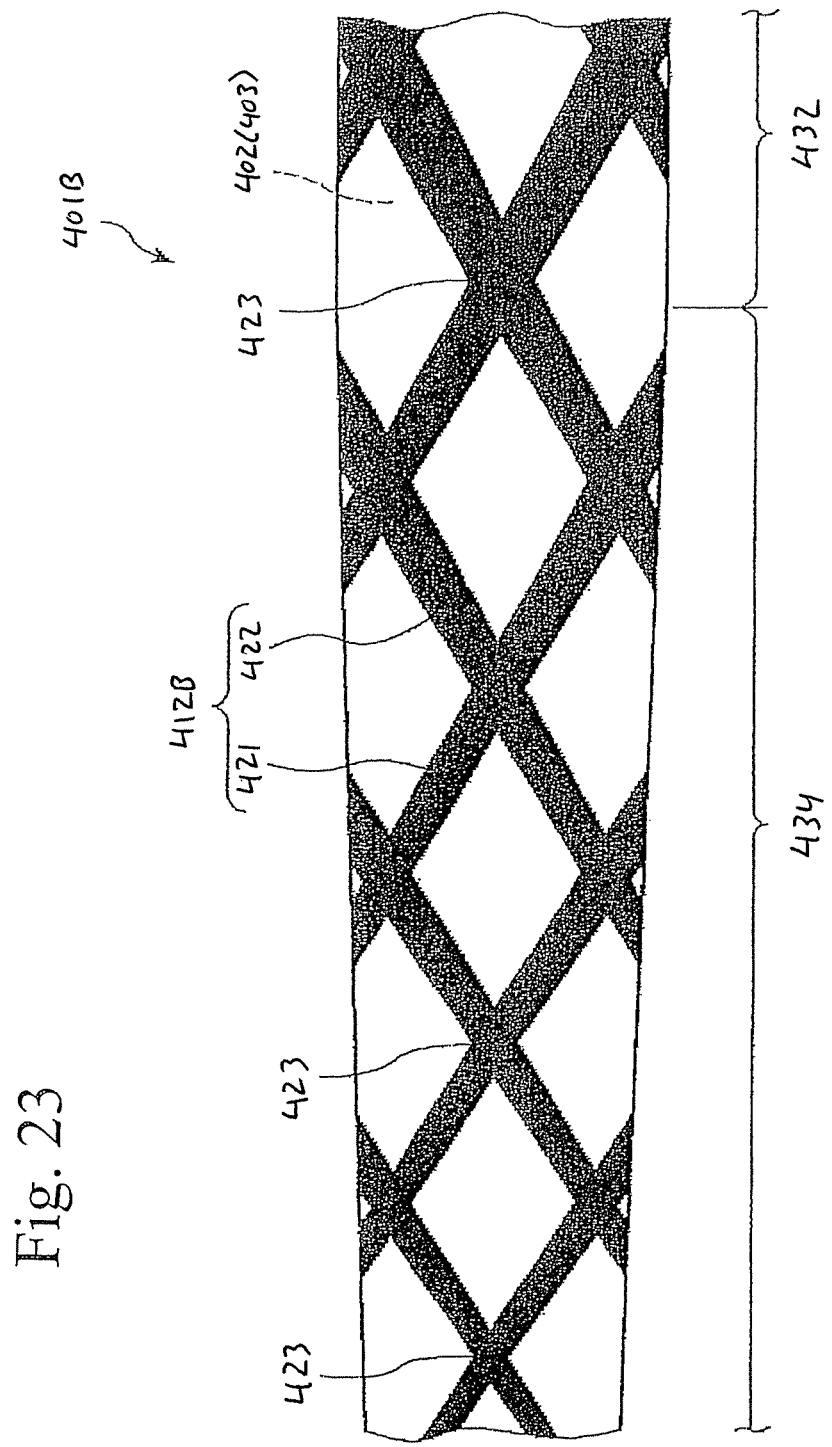
FIG. 23 is a side view showing a fourteenth embodiment of the guide wire disclosed here.

FIG. 23 is a side view of a fourteenth embodiment of the guide wire disclosed here. The following description of the guide wire embodiment shown in FIG. 23 will focus primarily upon differences between this embodiment and the FIGS. 16-21 embodiment described above. Features in this FIG. 23 embodiment that are the same as those in the earlier embodiment are identified by common reference numerals, and a detailed discussion of such features is not repeated here.

This embodiment is the same as the embodiment shown in FIGS. 16-21, except with respect to the conditions in which the first line-forming portion and the second line-forming portion are formed.

In the marker 412B of the guide wire 401B shown in FIG. 23, the widths of a first line-forming portion 421 and a second line-forming portion 422 are gradually decreased in the distal direction. The portion where the widths are gradually decreased is preferably formed at a tapered portion 434 of the wire body 402. By checking such a portion, it is possible to grasp that the wire body 402 is decreasing in diameter, and is high in flexibility, at the portion.

In addition, intersecting parts 423 differ in size in side view, according to the respective widths of the first line-forming portion 421 and the second line-forming portion 422. Such a configuration is effective in the case where the intersecting parts 423 are to be varied in size according to the outer diameter of the wire body 402. For example, as shown in FIG. 23, a configuration can be adopted in which the intersecting parts 423 are relatively smaller in size at the tapered portion 434 of the wire body 402, whereas the intersecting parts 423 are relatively larger in size at the body portion 432 which is greater in outer diameter than the tapered portion 434. This renders the intersecting parts 423 easy to view.

In connection with the embodiments shown in FIG. 16-23, the first line-forming portion and the second line-forming portion are not limited to those formed by drying a liquid material. For example, they may be formed by helically winding a belt-like or ribbon-like member.

The embodiments of the guide wire have been described in the context of the various illustrated embodiments. However, the present invention is not limited in this regard. The guide wires may be modified by replacing components with others having the same or similar functions, or by adding other components and processes.

The guide wire may have any two or more structures (features) in combination selected from the foregoing embodiments.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire positionable in a patient's body comprising:

an elongate wire member possessing a circumference and a longitudinal extent from a distal end of the wire member to a proximal end of the wire member;

an endoscopically-visible first line-forming marker portion and an endoscopically-visible second line-forming marking portion which are both positionable in the patient's body so that the first line-forming marker portion and the second line-forming marker portion positioned in the patient's body together with an endoscope are viewable outside the patient's body by way of the endoscope, the first line-forming marker portion and the second line-forming marker portion together indicating an intracorporeal position of the guide wire;

the first line-forming marker portion extending helically around the outer circumference of a first part of the longitudinal extent of the wire member in a first rotational direction, the first line-forming marker portion extending circumferentially around the wire member plural times, with adjacent windings of the first line-forming marker portion being spaced apart from one another;

the second line-forming marker portion extending helically around the outer circumference of the first part of the longitudinal extent of the wire member in a second rotational direction opposite the first rotational direction, the second line-forming marker portion extending circumferentially around the wire member plural times, with adjacent windings of the second line-forming marker portion being spaced apart from one another;

the first line-forming marker portion intersecting the second line-forming marker portion at a plurality of spaced apart intersecting locations, a height of the intersecting locations being greater than a height of the portions of the first line-forming portion and the second line-forming portion exclusive of the intersecting locations, and portions of the first part of the longitudinal extent of the wire member being uncovered by the first line-forming marker portion and the second line-forming marker portion; and a transparent cover layer covering the first line-forming marker portion and the second line-forming marker portion, the cover layer possessing an undulating outer surface.

2. The guide wire as set forth in claim 1, further comprising a primary layer of resin encircling the outer circumference of the wire member and positioned between the wire member and the first and second line-forming marker portions.

3. The guide wire as set forth in claim 2, wherein the primary layer and the first line-forming marker portion are visually differently colored of contrasting colors.

4. The guide wire as set forth in claim 1, wherein the first and second line-forming marker portions are visually differently colored.

5. The guide wire as set forth in claim 1, wherein the first line-forming marker portion possesses a pitch that varies in the longitudinal direction, and the second line-forming marker portion possesses a pitch that varies in the longitudinal direction.

6. The guide wire as set forth in claim 1, wherein the first line-forming marker portion possesses a width that varies in the longitudinal direction, and the second line-forming marker portion possesses a width that varies in the longitudinal direction.

7. The guide wire as set forth in claim 1, wherein the first and second line-forming marker portions are visually differently colored.

8. The guide wire as set forth in claim 1, wherein the wire member possesses a solid cross-section.

9. The guide wire as set forth in claim 1, further comprising a helical coil extending helically about the wire member at a distal end portion of the wire member, the helical coil being positioned entirely distally of both the first line-forming marker portion and the second line-forming marker portion.

10. The guide wire as set forth in claim 9, wherein at least a part of the helical coil is made of a radiopaque material.

11. The guide wire as set forth in claim 1, wherein the first line-forming marker portion and the second line-forming marker portion are differently colored so that the first line-forming marker portion and the second line-forming marker portion are visually distinguishable from one another.

12. The guide wire as set forth in claim 1, wherein the first line-forming marker portion is made of a material comprising resin and a pigment, the pigment providing the first line-forming marker portion with a color different from a color of the second line-forming marker portion.

13. The guide wire as set forth in claim 1, wherein the first line-forming marker portion and said portions of the first part of the longitudinal extent of the wire member uncovered by the first line-forming marker portion and the second line-forming marker portion possess different colors so that the first line-forming marker portion and said portions of the first part of the longitudinal extent of the wire member uncovered by the first line-forming marker portion and the second line-forming marker portion are visually distinguishable from one another.

14. The guide wire as set forth in claim 1, wherein the first line-forming marker portion and the second line-forming marker portion overlap one another at the plurality of spaced apart intersecting locations.

15. The guide wire as set forth in claim 1, wherein the height of the plurality of spaced apart intersecting locations is approximately 3 to 10 μm.

16. A guide wire positionable in a patient's body comprising:
an elongate wire member possessing a circumference and a longitudinal extent extending from a distal end of the wire member to a proximal end of the wire body;
an endoscopically-visible marker positionable in the patient's body so that the marker positioned in the patient's body with an endoscope are viewable outside the patient's body by way of the endoscope;
the marker being located on the wire member, extending along at least a portion of the longitudinal extent of the wire member and extending over an entirety of the circumference of the portion of the longitudinal extent of the wire member;
the marker comprising a first line-forming portion and a second line-forming portion which intersect each other at a plurality of locations so that the marker possesses an overall grid shaped arrangement of the first and second line-forming portions, a height of the locations being greater than a height of the portions of the first line-forming portion and the second line-forming portion exclusive of the locations;
wherein the marker is configured to ensure that when the guide wire is rotated about an axis of the guide wire, the rotation is visually confirmable extracorporeally with an endoscope; and
wherein the marker is configured to ensure that when the guide wire is axially moved, the axial movement is visually confirmable extracorporeally with the endoscope.

17. The guide wire as set forth in claim 16, wherein the marker is configured to ensure that, when the guide wire is axially moved or is rotated about the axis of the guide wire: i) axial movement of the guide wire is visually distinguishable extracorporeally with an endoscope from rotational movement of the guide wire; ii) rotational movement of the guide wire is visually distinguishable extracorporeally with an endoscope from axial movement of the guide wire; iii) axial movement of the guide wire in a distal direction is visually distinguishable extracorporeally with an endoscope from axial movement of the guide wire in a proximal direction; and iv) rotational movement of the guide wire in one rotational direction is visually distinguishable extracorporeally with an endoscope from rotational movement of the guide wire in an opposite rotational direction.

18. The guide wire as set forth in claim 16, wherein the first line-forming portion possesses a helical shape, and the second line-forming portion possesses a helical shape, with a winding direction of the helical shape of the first line-forming portion being in a direction opposite the winding direction of the helical shape of the second line-forming portion.

19. The guide wire as set forth in claim 18, wherein the first line-forming portion extends helically around the circumference of the wire member plural times, and wherein the second line-forming portion extends helically around the circumference of the wire member plural times.

20. The guide wire as set forth in claim 8, wherein the wire member possesses a solid cross-section.

21. The guide wire as set forth in claim 8, further comprising a helical coil extending helically about the wire member at a distal end portion of the wire member, the helical coil possessing a proximal-most end located distally of a distal-most end of both the first line-forming portion and the second line-forming portion.

22. The guide wire as set forth in claim 21, wherein at least a part of the helical coil is made of a radiopaque material.

23. The guide wire as set forth in claim 16, wherein the first line-forming marker portion and the second line-forming portion are differently colored so that the first line-forming portion and the second line-forming marker portion are visually distinguishable from one another.

24. The guide wire as set forth in claim 16, wherein the first line-forming marker portion possesses a color different from portions of the guide wire devoid of the first line-forming portion and the second line-forming marker portion so that the first line-forming portion is visually distinguishable from the portions of the guide wire devoid of the first line-forming portion and the second line-forming portion.

25. The guide wire as set forth in claim 16, wherein the height of the locations is approximately 3 to 10 μm.

26. A method of using a guidewire comprising:
inserting a guidewire together with an endoscope into a patient's body, the guidewire comprising: an elongate wire member possessing a circumference and a longitudinal extent extending from a distal end of the wire member to a proximal end of the wire member; and an endoscopically-visible marker located on the wire member, the endoscopically-visible marker extending along at least a portion of the longitudinal extent of the wire member and extending over an entirety of the circumference of the portion of the longitudinal extent of the wire member, the marker comprising first line-forming marker portion extending helically around the circumferential portion of the elongate wire in a first direction and the second line-forming marker portion extending helically around the circumferential portion of the elongate wire in a second direction opposite the first direction, the first line-forming marker portion intersecting the second line-forming marker portion at a plurality of spaced apart locations, a height of the spaced apart locations being greater than a height of the portions of the first line-forming portion and the second line-forming portion exclusive of the spaced apart locations;
rotating the guidewire while the first and second line-forming marker portions are in the patient's body to rotate the first line-forming marker portion and the second line-forming marker portion;
observing the rotation of the first and second line-forming marker portions in the patient's body using the endoscope also positioned in the patient's body;
axially moving the guidewire while the first and second line-forming marker portions are in the patient's body to axially move the first line-forming marker portion and the second line-forming marker portion; and observing the axial movement of the first and second line-forming marker portions in the patient's body using the endoscope also positioned in the patient's body.

27. The method of using a guidewire as set forth in claim 26, wherein the height of the plurality of spaced apart locations is approximately 3 to 10 μm.

\* \* \* \* \*